United States Patent
Lem

(10) Patent No.: US 10,889,558 B2
(45) Date of Patent: Jan. 12, 2021

(54) AMBER ODORANT

(71) Applicant: FIRMENICH SA, Satigny (CH)

(72) Inventor: George Lem, Satigny (CH)

(73) Assignee: Firmenich SA, Satigny (CH)

( * ) Notice: Subject to any disclaimer, the term of this patent is extended or adjusted under 35 U.S.C. 154(b) by 0 days.

(21) Appl. No.: 16/649,248

(22) PCT Filed: Nov. 28, 2018

(86) PCT No.: PCT/EP2018/082821
§ 371 (c)(1),
(2) Date: Mar. 20, 2020

(87) PCT Pub. No.: WO2019/106000
PCT Pub. Date: Jun. 6, 2019

(65) Prior Publication Data
US 2020/0299254 A1    Sep. 24, 2020

(30) Foreign Application Priority Data

Nov. 28, 2017   (EP) .................................... 17204079

(51) Int. Cl.
| | | |
|---|---|---|
| *A61K 8/18* | (2006.01) | |
| *A61K 8/00* | (2006.01) | |
| *A61Q 13/00* | (2006.01) | |
| *C07D 317/70* | (2006.01) | |
| *A61K 8/49* | (2006.01) | |
| *C11D 3/50* | (2006.01) | |

(52) U.S. Cl.
CPC .......... *C07D 317/70* (2013.01); *A61Q 13/00* (2013.01); *A61K 8/4973* (2013.01); *C11D 3/50* (2013.01)

(58) Field of Classification Search
CPC ............. A61K 8/18; A61K 8/00; A61Q 13/00
USPC ............................................ 512/12, 11, 8, 1
See application file for complete search history.

(56) References Cited

U.S. PATENT DOCUMENTS

| | | | |
|---|---|---|---|
| 4,396,670 A | 8/1983 | Sinclair | |
| 5,892,062 A | 4/1999 | Pickenhagen et al. | |
| 2012/0077722 A1* | 3/2012 | Dilk .................... | A61K 8/4973 510/103 |

FOREIGN PATENT DOCUMENTS

WO    0141915 A1    6/2001

OTHER PUBLICATIONS

International Search Report and Written Opinion for corresponding PCT/EP2018/082821, dated Feb. 26, 2019, 7 pages.
Martin et al., "Total Synthesis of Hematoporphyrin and Protoporphyrin: A Conceptually New Approach" Org. Proc. Res. & Dev., 2010, 14 799-804.
Bone et al. "Microencapsulated Fragrances in Melamine Formaldehyde Resins" Chimia, 2011, vol. 65, No. 3, 177-181.
Detrich et al., "Amino Resin Microcapsules" III. Release Properties, Acta Polymerica, 40 (1989) No. 11, 683-690.
Detrich et al., "Amino Resin Microcapsules" I. Lititure and Patent Review, Acta Polymerica, 40 (1989) No. 4, 243-251.
Detrich et al., "Amino Resin Microcapsules" II. Preparation and Morphology, Acta Polymerica, 40 (1989) No. 5, 325-331.
Detrich et al., "Amino Resin Microcapsules" Acta Polymerica, 40 (1989) No. 2, 91-95.
Lee et al. "Microencapsulation of Fragrant Oil Via in Situpolymerization: Effects of PH and Melamineformaladehyde Molor Ratio" Journal of Microencapsulation, 2002, vol. 19, pp. 559-569.

* cited by examiner

*Primary Examiner* — Jessica Whiteley
(74) *Attorney, Agent, or Firm* — Armstrong Teasdale LLP

(57) ABSTRACT

Described herein is a compound of formula (I)

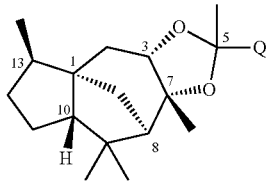

(I)

in the form of any one of its stereoisomers or a mixture thereof, and where the Q group represents a —CH═CH—CH₃ group or a —C≡C—CH₃ group. Also described herein is a method of using a compound of formula (I), the method including using the compound of formula (I) as part of a perfuming composition or as part of a perfumed consumer product.

17 Claims, No Drawings

AMBER ODORANT

CROSS-REFERENCE TO RELATED APPLICATIONS

This application is a U.S. National Phase Application of PCT/EP2018/082821, filed Nov. 28, 2018, which claims the benefit of priority to European Patent Application No. 17204079.2, filed Nov. 28, 2017, the entire contents of which are hereby incorporated by reference herein.

TECHNICAL FIELD

The present invention relates to the field of perfumery. More particularly, it concerns the compound of formula (I) as defined herein below, and its uses as perfuming ingredients. Therefore, following what is mentioned herein, the present invention comprises the invention compound as part of a perfuming composition or of a perfumed consumer product.

BACKGROUND

One of the most sought ingredients in the perfumery field is the ones imparting an ambergris impression. Said note, impacting in particular the bottom note by providing more volume and supporting top note of a perfuming composition, is very appreciated and used in a multitude of perfumed consumer products. Originally, Ambergris is a natural product produced in the digestive system of sperm whales which is very rare and very expensive.

So, there is a need to develop a less expensive synthetic alternative to natural ambergris conferring a woody and amber odor notes with low volatility to affect the top and the bottom note and being as close as possible to the natural ambergris note also called white amber note while maintaining or even improving the tenacity/substantivity.

US 20120077722 reports, as a compound imparting said olfactive properties, a mixture of (1R,3S,5R,7R,8R,10S,13R)-5,7,9,9,9,13-pentamethyl-5-propyl-4,6-dioxatetracyclo[6.5.1.0$^{1,10}$.0$^{3,7}$]tetradecane and (1R,3S,5S,7R,8R,10S,13R)-5,7,9,9,13-pentamethyl-5-propyl-4,6-dioxatetracyclo [6.5.1.0$^{1,10}$.0$^{3,7}$]tetradecane. In particular, the isomer (1R,3S,5R,7R,8R,10S,13R)-5,7,9,9,9,13-pentamethyl-5-propyl-4,6-dioxatetracyclo[6.5.1.0$^{1,10}$.0$^{3,7}$]tetradecane is reported to possess a strong odor of ambergris and wood and high substantivity. This mixture is one of the most promising replacer to ambergris.

The present invention provides new compounds with the advantages of the prior art while improving the performance. The prior art document mentioned above does not report or suggest any organoleptic properties of the compounds of formula (I), or any use of said compounds in the field of perfumery.

SUMMARY OF THE INVENTION

The invention relates to compound of formula (I) imparting ambergris with the highest performance in term of power and tenacity.

So, a first object of the present invention is a compound of formula

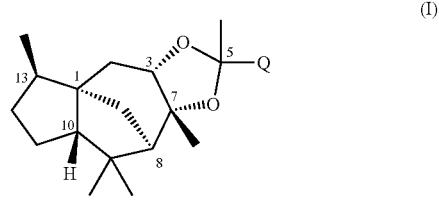

in the form of any one of its stereoisomers or as a mixture thereof, and wherein Q group represents a —CH=CH—CH$_3$ group or a —C≡C—CH$_3$ group.

A second object of the present invention is the use as perfuming ingredient of a compound of formula (I) as defined above.

A third object of the present invention is a method to confer, enhance, improve or modify the odor properties of a perfuming composition or of a perfumed article, which method comprises adding to said composition or article an effective amount of at least a compound of formula (I) as defined above.

Another object of the present invention is a perfuming composition comprising i) at least one compound of formula (I), as defined above;

ii) at least one ingredient selected from the group consisting of a perfumery carrier and a perfumery base; and iii) optionally at least one perfumery adjuvant.

Another object of the present invention is a perfumed consumer product comprising at least one compound of formula (I), as defined above or a perfuming composition as defined above.

A last object of the present invention is a compound of formula

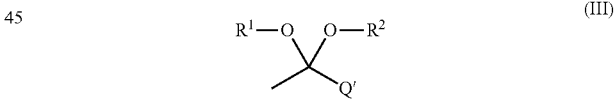

in the form of any one of its stereoisomers or as a mixture thereof, and wherein Q' represents a —CH=CH—CH$_3$ group or a —C≡C—CH$_3$ group; and R$^1$ and R$^2$ group represent, independently from each other, a C$_{1-3}$ alkyl group or R$^1$ and R$^2$ group represent, when taken together, a C$_{2-3}$ alkanediyl; provided that 4,4-diethoxy-2-pentyne, 2-Methyl-2-(1-propyn-1-yl)-1,3-dioxolane and 2-methyl-2-(1-propenyl) 1,3-Dioxolane are excluded.

DESCRIPTION OF THE INVENTION

Surprisingly, it has now been discovered that compound of formula (I) imparts the most powerful and linear woody and amber note compared to the synthetic ingredient normally used in this goal. This compound has also never been disclosed.

Herein disclosed is a compound of formula

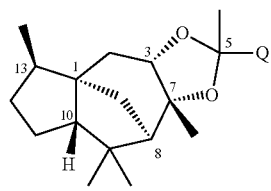

(I)

in the form of any one of its stereoisomers or as a mixture thereof, and wherein Q group represents a —CH=CH—CH$_3$ group, a —CH$_2$—CH=CH$_2$ group, a —C≡C—CH$_3$ group, a —CH$_2$—C≡CH group, a cyclopropyl group, or a 2-methylcyclopropyl group.

A first object of the present invention is a compound of formula

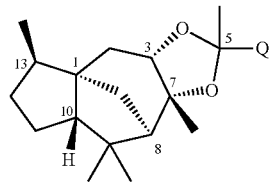

(I)

in the form of any one of its stereoisomers or as a mixture thereof, and wherein Q group represents a —CH=CH—CH$_3$ group or a —C≡C—CH$_3$ group.

Said compounds can be used as perfuming ingredients, for instance to impart odor notes of the woody and amber type.

For the sake of clarity, by the expression "any one of its stereoisomers or as a mixture thereof", or the similar, it is meant the normal meaning understood by a person skilled in the art, i.e. that the invention compound can be a pure or be in the form of a mixture of enantiomers or diastereoisomers (e.g. the carbon 5 could be R, S or a mixture thereof). According to any one of the above embodiments of the invention, the stereocenter of carbon 5 may be R or S or a mixture thereof. The other stereocenters have a fix stereochemistry; i.e. the carbon 1 of compound of formula (I) has an absolute R configuration, the carbon 3 of compound of formula (I) has an absolute S configuration, the carbon 7 of compound of formula (I) has an absolute R configuration, the carbon 8 of compound of formula (I) has an absolute R configuration, the carbon 10 of compound of formula (I) has an absolute S configuration and the carbon 13 of compound of formula (I) has an absolute R configuration. According to any one of the above embodiments of the invention, the compound of formula (I) is in the form of a mixture of isomers comprising at least 55% of isomers with a R configuration on carbon 5 and at most 45% of isomers with a S configuration on carbon 5. Preferably, the compound of formula (I) is in the form of a mixture of isomers comprising at least 70% of isomers with a R configuration on carbon 5 and at most 30% of isomers with a S configuration on carbon 5. Even more preferably, the compound of formula (I) is in the form of a mixture of isomers comprising at least 80% of isomers with a R configuration on carbon 5 and at most 20% of isomers with a S configuration on carbon 5.

According to any one of the above embodiments of the invention, said compound can be in the form of its E or Z isomer or of a mixture thereof, e.g. the invention comprises compositions of matter consisting of one or more compounds of formula (I), having the same chemical structure but differing by the configuration of the double bond. In particular, compound (I) can be in the form of a mixture consisting of isomers E and Z and wherein said isomer E represents at least 0.5% of the total mixture, or even at least least 50% of the total mixture, or even at least 75% (i.e a mixture E/Z comprised between 75/25 and 100/0). Preferably, compound of formula (I) is in the form of an E isomer.

According to any one of the above embodiments of the invention, said compounds (I) are C$_{20}$ compounds.

According to any one of the above embodiments of the invention, the compound of the present invention is of formula

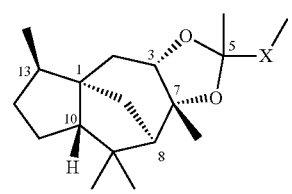

(II)

in the form of any one of its stereoisomers or as a mixture thereof, and wherein X group represents a —CH=CH— group or a —C≡C— group.

Preferably, the X group may be a —CH=CH group. In other words, preferably, the Q group may be a —CH=CH—CH$_3$ group As specific examples of the invention's compounds, one may cite, as non-limiting example, 5,7,9,9,13-pentamethyl-5-[(1E)-1-propen-1-yl]-4,6-dioxatetracyclo[6.5.1.0$^{1,10}$.0$^{3,7}$] tetradecane in a form of a mixture comprising the diastereoisomers (1R,3S,5R,7R,8R,10S,13R) and (1R,3S,5S,7R,8R,10S,13R) in a respective ratio of 85:15 which is characterized by very powerful woody, dry and amber note. Said compound also possesses limbanol and cedar connotation.

As other example, one may cite 5,7,9,9,13-pentamethyl-5-[(1E)-1-propen-1-yl]-4,6-dioxatetracyclo[6.5.1.0$^{1,10}$.0$^{3,7}$] tetradecane in a form of a mixture comprising the diastereoisomers (1R,3S,5R,7R,8R,10S,13R) and (1R,3S,5S,7R,8R,10S,13R) in a respective ratio of 98:02, which possesses an odor similar to the one mentioned above while maintaining the power and substantively.

As other example, one may cite (–)-(1R,3S,5R,7R,8R,10S,13R)-5,7,9,9,13-pentamethyl-5-(1-propyn-1-yl)-4,6-dioxatetracyclo[6.5.1.0$^{1,10}$.0$^{3,7}$]tetradecane which possesses an odor similar to the one mentioned above slightly less powerful.

The invention's compound is very powerful. All of the comparative compounds cited above, being structurally close to the invention compound, impart a woody and amber note however being less strong.

TABLE 1

Comparative compounds and their odor properties

| Compound structure and name | Odor notes |
|---|---|
| [structure] [structure] 7,9,9,13-tetramethyl-5-(1-propen-1-yl)-4,6-dioxatetracyclo[6.5.1.0$^{1,10}$.0$^{3,7}$]tetradecane in a form of a mixture comprising the diastereoisomers (1R,3S,5R,7R,8R,10S,13R) and (1R,3S,5S,7R,8R,10S,13R) in a respective ratio of 8:92 or 41:59 | woody, dry, cedar, ambery, weaker than the invention's compound |
| [structure] [structure] 7,9,9,13-tetramethyl-5-(2-methyl-1-propen-1-yl)-4,6-dioxatetracyclo[6.5.1.0$^{1,10}$.0$^{3,7}$]tetradecane in a form of a mixture comprising the diastereoisomers (1R,3S,5R,7R,8R,10S,13R) and (1R,3S,5S,7R,8R,10S,13R) in a respective ratio of 12:88 | woody, ambery, weaker than the invention's compound |
| [structure] [structure] 7,9,9,13-tetramethyl-5-(3-buten-1-yl)-4,6-dioxatetracyclo[6.5.1.0$^{1,10}$.0$^{3,7}$]tetradecane in a form of a mixture comprising the diastereoisomers (1R,3S,5R,7R,8R,10S,13R) and (1R,3S,5S,7R,8R,10S,13R) in a respective ratio of 9:91 | Woody, weaker than invention's compound |
| [structure] [structure] 5-[(2E)-2-buten-2-yl]-5,7,9,9,13-pentamethyl-4,6-dioxatetracyclo[6.5.1.0~$^{1,10}$~.0~$^{3,7}$~]tetradecane in a form of a mixture comprising the diastereoisomers (1R,3S,5R,7R,8R,10S,13R) and (1R,3S,5S,7R,8R,10S,13R) in a respective ratio of 78:22 | Weakly woody |
| [structure] [structure] 5-isopropenyl-5,7,9,9,13-pentamethyl-4,6-dioxatetracyclo[6.5.1.0~$^{1,10}$~.0~$^{3,7}$~]tetradecane in a form of a mixture comprising the diastereoisomers (1R,3S,5R,7R,8R,10S,13R) and (1R,3S,5S,7R,8R,10S,13R) in a respective ratio of 79:21 | Very weak, vaguely woody |
| [structure] [structure] 5,7,9,9,13-pentamethyl-5-(2-methyl-1-propen-1-yl)-4,6-dioxatetracyclo [6.5.1.0~$^{1,10}$~.0~$^{3,7}$~]tetradecane in a form of a mixture comprising the diastereoisomers (1R,3S,5R,7R,8R,10S,13R) and (1R,3S,5S,7R,8R,10S,13R) in a respective ratio of 67:33 | Very weak, vaguely woody-dry |

TABLE 1-continued

Comparative compounds and their odor properties

| Compound structure and name | Odor notes |
|---|---|
| 5,7,9,9,13-pentamethyl-5-vinyl-4,6-dioxatetracyclo[6.5.1.0~1,10~.0~3,7~]tetradecane in a form of a mixture comprising the diastereoisomers (1R,3S,5R,7R,8R,10S,13R) and (1R,3S,5S,7R,8R,10S,13R) in a respective ratio of 88:12 | Woody, dry, weaker than the invention's compound |
| 5-ethyl-7,9,9,13-tetramethyl-5-[(1E)-1-propen-1-yl]-4,6-dioxatetracyclo[6.5.1.0$^{1,10}$.0$^{3,7}$]tetradecane in a form of a mixture comprising the diastereoisomers (1R,3S,5R,7R,8R,10S,13R) and (1R,3S,5S,7R,8R,10S,13R) in a respective ratio of 92:8 | Woody, dry, weaker than the invention's compound |
| 5-ethyl-7,9,9,13-tetramethyl-5-vinyl-4,6-dioxatetracyclo[6.5.1.0$^{1,10}$.0$^{3,7}$]tetradecane in a form of a mixture comprising the diastereoisomers (1R,3S,5R,7R,8R,10S,13R) and | Woody, cedar, dry, weaker than the invention's compound |

TABLE 1-continued

Comparative compounds and their odor properties

| Compound structure and name | Odor notes |
|---|---|
| (1R,3S,5S,7R,8R,10S,13R) in a respective ratio of 59:41 | |
| 5,7,9,9,13-pentamethyl-5-vinyl-4,6-dioxatetracyclo[6.5.1.0$^{1,10}$.0$^{3,7}$]tetradecane in a form of a mixture comprising the diastereoisomers (1R,3S,5R,7R,8R,10S,13R) and (1R,3S,5S,7R,8R,10S,13R) in a respective ratio of 68:32 | Very weak, vaguely woody-dry |
| 7',9',9',13'-tetramethyl-4',6'-dioxaspiro[cyclohexane-1,5'-tetracyclo[6.5.1.0$^{1,10}$.0$^{3,7}$]tetradecane]-2-ene in a form of a mixture comprising the diastereoisomers (1R,1'R,3'S,7'R,8'R,10'S,13'R) and (1S,1'R,3'S,7'R,8'R,10'S,13'R) in a respective ratio of 59:41 | Very weak, vaguely woody |
| | Woody, ambery, weaker than the invention's compound |

TABLE 1-continued

Comparative compounds and their odor properties

| Compound structure and name | Odor notes |
|---|---|
| 5-(3-buten-1-yl)-5,7,9,9,13-pentamethyl-4,6-dioxatetracyclo[6.5.1.0$^{1,10}$.0$^{3,7}$]tetradecane in a form of a mixture comprising the diastereoisomers (1R,3S,5R,7R,8R,10S,13R) and (1R,3S,5S,7R,8R,10S,13R) in a respective ratio of 82:18 | |
| (1R,3S,5R,7R,8R,10S,13R)-5-ethynyl-5,7,9,9,13-pentamethyl-4,6-dioxatetracyclo[6.5.1.0$^{1,10}$.0$^{3,7}$]tetradecane | Very weak, woody-dry |
| 5,7,9,9,13-pentamethyl-5-[2-methylcyclopropyl]-4,6-dioxatetracyclo[6.5.1.0~1,10~.0~3,7~]tetradecane in a form of a mixture comprising the diastereoisomers (1R,3S,5R,7R,8R,10S,13R) and (1R,3S,5S,7R,8R,10S,13R) in a respective ratio of 91:9 | Woody, ambery, very weaker than the invention's compound |
| (1R,3S,5R,7R,8R,10S,13R)-5-cyclopropyl-5,7,9,9,13-pentamethyl-4,6-dioxatetracyclo[6.5.1.0$^{1,10}$.0$^{3,7}$]tetradecane | Woody, ambery, very weaker than the invention's compound |

According to any one of the above embodiments of the invention, the compound of formula (I) may be selected from the group consisting of (1R,3S,5R,7R,8R,10S,13R)-5,7,9,9,13-pentamethyl-5-[1-propen-1-yl]-4,6-dioxatetracyclo[6.5.1.0$^{1,10}$.0$^{3,7}$]tetradecane, (1R,3S,5S,7R,8R,10S,13R)-5,7,9,9,13-pentamethyl-5-[1-propen-1-yl]-4,6-dioxatetracyclo[6.5.1.0$^{1,10}$.0$^{3,7}$]tetradecane, or a mixture thereof; (1R,3S,5R,7R,8R,10S,13R)-5,7,9,9,13-pentamethyl-5-[(1E)-1-propen-1-yl]-4,6-dioxatetracyclo[6.5.1.0$^{1,10}$.0$^{3,7}$]tetradecane, (1R,3S,5S,7R,8R,10S,13R)-5,7,9,9,13-pentamethyl-5-[(1E)-1-propen-1-yl]-4,6-dioxatetracyclo[6.5.1.0$^{1,10}$.0$^{3,7}$]tetradecane, or a mixture thereof; (1R,3S,5R,7R,8R,10S,13R)-5,7,9,9,13-pentamethyl-5-[1-propyn-1-yl]-4,6-dioxatetracyclo[6.5.1.0$^{1,10}$.0$^{3,7}$]tetradecane, (1R,3S,5S,7R,8R,10S,13R)-5,7,9,9,13-pentamethyl-5-[1-propyn-1-yl]-4,6-dioxatetracyclo[6.5.1.0$^{1,10}$.0$^{3,7}$]tetradecane or a mixture thereof. Preferably, the compound of formula (I) may be selected from the group consisting of (1R,3S,5R,7R,8R,10S,13R)-5,7,9,9,13-pentamethyl-5-[(1E)-1-propen-1-yl]-4,6-dioxatetracyclo[6.5.1.0$^{1,10}$.0$^{3,7}$]tetradecane, (1R,3S,5S,7R,8R,10S,13R)-5,7,9,9,13-pentamethyl-5-[(1E)-1-propen-1-yl]-4,6-dioxatetracyclo[6.5.1.0$^{1,10}$.0$^{3,7}$]tetradecane, or a mixture thereof.

When the odor of the invention's compound is compared with the prior art mixture comprising (1R,3S,5R,7R,8R,10S,13R)-5,7,9,9,13-pentamethyl-5-propyl-4,6-dioxatetracyclo[6.5.1.0$^{1,10}$.0$^{3,7}$]tetradecane and (1R,3S,5S,7R,8R,10S,13R)-5,7,9,9,13-pentamethyl-5-propyl-4,6-dioxatetracyclo[6.5.1.0$^{1,10}$.0$^{3,7}$]tetradecane as reported in example I of US 20120077722, then the invention's compounds possesses a similar white amber and woody odor reminiscent of Ambergris but distinguishing themselves by woody/limbanol note. Moreover, the invention's compound imparts a clearly stronger and more substantive note. The olfactive profile of the invention's compound is more linear with lower fluctuation along the time compared to the prior art. In other words, the invention's compound confers white amber note characteristic of the prior art while improving the strength and the tenacity/substantivity of the organoleptic note. The invention compound clearly overperforms compared to structurally closed compounds or compared to prior art compounds belonging to the same organoleptic family.

Said differences lend the invention's compounds to be used in a lower concentration than the prior art compounds to impart a similar organoleptic impression.

As mentioned above, the invention concerns the use of a compound of formula (I) as a perfuming ingredient. In other words, it concerns a method or a process to confer, enhance, improve or modify the odor properties of a perfuming composition or of a perfumed article or of a surface, which method comprises adding to said composition or article an effective amount of at least a compound of formula (I), e.g. to impart its typical note. Understood that the final hedonic effect may depend on the precise dosage and on the organoleptic properties of the invention's compound, but anyway the addition of the invention's compound will impart to the final product its typical touch in the form of a note, touch or aspect depending on the dosage.

By "use of a compound of formula (I)" it has to be understood here also the use of any composition containing a compound (I) and which can be advantageously employed in the perfumery industry.

Said compositions, which in fact can be advantageously employed as perfuming ingredients, are also an object of the present invention.

Therefore, another object of the present invention is a perfuming composition comprising:
i) as a perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" it is meant here a material which is practically neutral from a perfumery point of view i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples, solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. The use of solid carrier is of current use in the art and a person skilled in the art knows how to reach the desired effect. However by way of non-limiting example of solid carriers, one may cite absorbing gums or polymers or inorganic material, such as porous polymers, cyclodextrins, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs-und Geliermittel in Lebensmitteln, Band 2 der Schriftenreihe Lebensmittelchemie, Lebensmittelqualität, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation technique.

As non-limiting examples of solid carriers, one may cite in particular the core-shell capsules with resins of aminoplast, polyamide, polyester, polyurea or polyurethane type or a mixture thereof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine such as urea, benzoguanamine, glycoluryl, melamine, methylol melamine, methylated methylol melamine, guanazole and the like, as well as mixtures thereof. Alternatively one may use preformed resins alkylated polyamines such as those commercially available under the trademark Urac® (origin: Cytec Technology Corp.), Cymel® (origin: Cytec Technology Corp.), Urecoll® or Luracoll® (origin: BASF).

Others resins one are the ones produced by the polycondensation of an a polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate.

Some of the seminal literature related to the encapsulation of perfumes by polycondensation of amino resins, namely melamine based resins with aldehydes includes represented by articles such as those published by K. Dietrich et al. Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors have enriched the literature in this field and it would be impossible to cover all published developments here, but the general knowledge in encapsulation technology is very significant. More recent publications of pertinency, which disclose suitable uses of such microcapsules, are represented for example by the article of H. Y. Lee et al. Journal of Microencapsulation, 2002, vol. 19, pages 559-569, international patent publication WO 01/41915 or yet the article of S. Bône et al. Chimia, 2011, vol. 65, pages 177-181.

By "perfumery base" what is meant here is a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin.

In particular one may cite perfuming co-ingredients which are commonly used in perfume formulations, such as:
  Aldehydic ingredients: decanal, dodecanal, 2-methyl-undecanal, 10-undecenal, octanal and/or nonenal;
  Aromatic-herbal ingredients: eucalyptus oil, camphor, eucalyptol, menthol and/or alpha-pinene;

Balsamic ingredients: coumarine, ethylvanillin and/or vanillin;

Citrus ingredients: dihydromyrcenol, citral, orange oil, linalyl acetate, citronellyl nitrile, orange terpenes, limonene, 1-P-menthen-8-yl acetate and/or 1,4(8)-P-menthadiene;

Floral ingredients: Methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, hexyl salicylate, 3,7-dimethyl-1,6-nonadien-3-ol, 3-(4-isopropylphenyl)-2-methylpropanal, verdyl acetate, geraniol, P-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-P-menthanol, Propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 4-phenyl-2-butanone, isononyle acetate, 4-(1,1-dimethylethyl)-1-cyclohexyl acetate, verdyl isobutyrate and/or mixture of methylionones isomers, 2-Methyl-3-(3-tertbutylphenyl)propanal, 2,5,7,7-Tetramethyl-octanal, 4-(1,1-Dimethylethyl)phenylpropanal, 3-(4-Isopropylphenyl)propanal, Octahydro-8,8-dimethylnaphthalene-2-carboxaldehyd, Octahydro-4,7-methanoindanilydenebutanal, beta-Methyl-3-(1-methylethyl)phenylpropanal, 2-Methyl-3-(3,4-methylendioxyphenyl)propanal, 7-Hydroxy-3,7-dimethyloctanal, 4-(4-Hydroxy-4-methylpentyl)-3-cyclohexen-1-carboxaldehyd, 2,2-Dimethyl-3-(3-methylphenyl)propanol, cis-4-(1-methylethyl) cyclohexanmethanol, 1-(4-Isopropylcyclohexyl) ethanol, 3-Methyl-4-phenylbutan-2-ol, Dimethylphenylpropanol, 2-Methyl-3-(4-(2-methylpropyl)phenyl)propanal, 3-(4-Isobutylphenyl)-2-methylpropanal, 3,4-Dioxy(cycloacetonyl)toluol, 3-(1-Ethoxyethoxy)-3,7-dimethyl-1,6-octadien, alpha,alpha-Dimethyl-4-ethylphenylpropanal, gamma-Methylphenylpentanal;

Fruity ingredients: gamma undecalactone, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate and/or diethyl 1,4-cyclohexane dicarboxylate;

Green ingredients: 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;

Musk ingredients: 1,4-dioxa-5,17-cycloheptadecanedione, pentadecenolide, 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-1'-cyclohexyl)ethoxy]-2-methylpropyl propanoate, pentadecanolide and/or (1S,1'R)-[1-(3',3'-Dimethyl-1'-cyclohexyl)ethoxycarbonyl]methyl propanoate;

Woody ingredients: 1-(octahydro-2,3,8,8-tetramethyl-2-naphtalenyl)-1-ethanone, patchouli oil, terpenes fractions of patchouli oil, (1'R,E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, Methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b]furan and any of its stereoisomers, heliotropin, anisic aldehyde, eugenol, cinnamic aldehyde, clove oil, 3-(1,3-benzodioxol-5-yl)-2-methylpropanal and/or 3-(3-isopropyl-1-phenyl)butanal.

Preferably, the invention's compounds may be used with musky, woody, ambery powdery co-ingredients, in particular with pentadecenolide, 1-(octahydro-2,3,8,8-tetramethyl-2-naphtalenyl)-1-ethanone, dodecahydro-3a,6,6,9a-tetramethyl-naphtho[2,1-b]furan and any of its stereoisomers, mixture of methylionones isomers, Methyl 2,4-dihydroxy-3,6-dimethylbenzoate, 3,3-dimethyl-5-(2,2,3-trimethyl-3-cyclopenten-1-yl)-4-penten-2-ol, mixture of 1-[2,6,10-trimethyl-1,5,9-cyclododecatrien-1-yl]ethanone, 1-[-4,8-dimethyl-12-methylene-4,8-cyclododecadien-1-yl]ethanone and 1-[-2,6,10-trimethyl-2,5,9-cyclododecatrien-1-yl]ethanone or vetiver oil.

A perfumery base according to the invention may not be limited to the above mentioned perfuming co-ingredients, and many other of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming composition cannot be exhaustive, but it has to be mentioned that said ingredients are well known to a person skilled in the art. One may cite as specific non-limiting examples the following: viscosity agents (e.g. surfactants, thickeners, gelling and/or rheology modifiers), stabilizing agents (e.g. preservatives, antioxidant, heat/light and or buffers or chelating agents, such as BHT), coloring agents (e.g. dyes and/or pigments), preservatives (e.g. antibacterial or antimicrobial or antifungal or anti irritant agents), abrasives, skin cooling agents, fixatives, insect repellants, ointments, vitamins and mixtures thereof.

It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least one compound of formula (I) and at least one perfumery carrier consists of a particular embodiment of the invention as well as a perfuming composition comprising at least one compound of formula (I), at least one perfumery carrier, at least one perfumery base, and optionally at least one perfumery adjuvant.

According to a particular embodiment, the compositions mentioned above, comprise more than one compound of formula (I) and enable the perfumer to prepare accords or perfumes possessing the odor tonality of various compounds of the invention, creating thus new building block for creation purposes.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

The invention's compound can also be advantageously used in all the fields of modern perfumery, i.e. fine or functional perfumery, to positively impart or modify the odor of a consumer product into which said compound (I) is added. Consequently, another object of the present invention consists of by a perfumed consumer product comprising, as a perfuming ingredient, at least one compound of formula (I), as defined above.

The invention's compound can be added as such or as part of an invention's perfuming composition.

For the sake of clarity, "perfumed consumer product" is meant to designate a consumer product which delivers at least a pleasant perfuming effect to the surface or space to which it is applied (e.g. skin, hair, textile, or home surface). In other words, a perfumed consumer product according to the invention is a perfumed consumer product which comprises a functional formulation, as well as optionally additional benefit agents, corresponding to the desired consumer product, and an olfactive effective amount of at least one invention's compound. For the sake of clarity, said perfumed consumer product is a non-edible product.

The nature and type of the constituents of the perfumed consumer product do not warrant a more detailed description here, which in any case would not be exhaustive, the skilled person being able to select them on the basis of his general knowledge and according to the nature and the desired effect of said product.

Non-limiting examples of suitable perfumed consumer product include a perfume, such as a fine perfume, a splash or eau de parfum, a cologne or a shave or after-shave lotion; a fabric care product, such as a liquid or solid detergent, a fabric softener, a liquid or solid scent booster, a fabric refresher, an ironing water, a paper, a bleach, a carpet cleaner, a curtain-care product; a body-care product, such as a hair care product (e.g. a shampoo, a coloring preparation or a hair spray, a color-care product, a hair shaping product, a dental care product), a disinfectant, an intimate care product; a cosmetic preparation (e.g. a skin cream or lotion, a vanishing cream or a deodorant or antiperspirant (e.g. a spray or roll on), a hair remover, a tanning or sun or after sun product, a nail product, a skin cleansing, a makeup); or a skin-care product (e.g. a soap, a shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furnisher care product, a wipe, a dish detergent or a hard-surface (e.g. a floor, bath, sanitary or a window-cleaning) detergent; a leather care product; a car care product, such as a polish, a wax or a plastic cleaner.

Some of the above-mentioned perfumed consumer products may represent an aggressive medium for the invention's compounds, so that it may be necessary to protect the latter from premature decomposition, for example by encapsulation or by chemically binding it to another chemical which is suitable to release the invention's ingredient upon a suitable external stimulus, such as an enzyme, light, heat or a change of pH.

The proportions in which the compounds according to the invention can be incorporated into the various aforementioned products or compositions vary within a wide range of values. These values are dependent on the nature of the article to be perfumed and on the desired organoleptic effect as well as on the nature of the co-ingredients in a given base when the compounds according to the invention are mixed with perfuming co-ingredients, solvents or additives commonly used in the art.

For example, in the case of perfuming compositions, typical concentrations are in the order of 0.0001% to 10% by weight, or even more, of the compounds of the invention based on the weight of the composition into which they are incorporated. In the case of perfumed consumer product, typical concentrations are in the order of 0.00001% to 1% by weight, or even more, of the compounds of the invention based on the weight of the consumer product into which they are incorporated.

The invention's compounds or analogues can be prepared by methods known by the person skilled in the art such as by reacting cedrenediol which is commercially available with compound of formula

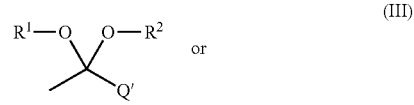

(III)

or

(IV)

in the form of any one of its stereoisomers or as a mixture thereof, and wherein Q' represents a —CH=CH—CH$_3$ group, a —CH$_2$—CH=CH$_2$ group, a —C≡C—CH$_3$ group, a —CH$_2$—C≡CH group, a cyclopropyl group, or a 2-methylcyclopropyl group; and $R^1$ and $R^2$ group represent, independently from each other a C$_{1-3}$ alkyl group or $R^1$ and $R^2$ group represent, when taken together, a C$_{2-3}$ alkanediyl; in the presence of an acid.

Compound of formula (III) is novel, so another object of the present invention is a compound of formula

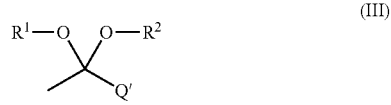

(III)

in the form of any one of its stereoisomers or as a mixture thereof, and wherein Q' represents a —CH=CH—CH$_3$ group, a —CH$_2$—CH=CH$_2$ group, a —C≡C—CH$_3$ group, a —CH$_2$—C≡CH group, or a 2-methylcyclopropyl group; and $R^1$ and $R^2$ group represent, independently from each other, a C$_{1-3}$ alkyl group or $R^1$ and $R^2$ group represent, when taken together, a C$_{2-3}$ alkanediyl; provided that 4,4-diethoxy-2-pentyne, 4,4-Dimethoxy-1-pentene, 4,4-diethoxy- 1-pentyne, 2-Methyl-2-(1-propyn-1-yl)-1,3-dioxolane, 2-Methyl-2-(2-propyn-1-yl)-1,3-dioxolane, 2-Methyl-2-(2-propen-1-yl)-1,3-dioxolane, 2-methyl-2-(1-propenyl) 1,3-Dioxolane, and 4-ethoxy-4-methoxy-1-pentene are excluded.

According to any above embodiment, the compound of formula (III) is of formula

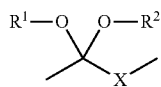

(IV)

in the form of any one of its stereoisomers or as a mixture thereof, and wherein X, $R^1$ and $R^2$ group have the same meaning as defined above; provided that 4,4-diethoxy-2-pentyne, 2-Methyl-2-(1-propyn-1-yl)-1,3-dioxolane and 2-methyl-2-(1-propenyl) 1,3-Dioxolane are excluded.

Preferably, Q' may be a —CH=CH—CH$_3$ group or a —C≡C—CH$_3$ group. In other words, X may be a —CH=CH— group or a —C≡C— group.

EXAMPLES

The invention will now be described in further detail by way of the following examples, wherein the abbreviations have the usual meaning in the art, the temperatures are indicated in degrees centigrade (° C.); the NMR spectral data were recorded in CDCl$_3$ (if not stated otherwise) with a 360 or 400 MHz machine for $^1$H and $^{13}$C, the chemical shifts S are indicated in ppm with respect to TMS as standard, the coupling constants J are expressed in Hz.

Example 1

Synthesis of 5,7,9,9,13-pentamethyl-5-[(1E)-1-propen-1-yl]-4,6-dioxatetracyclo[6.5.1.0$^{1,10}$.0$^{3,7}$]tetradecane in a Form of a Mixture Comprising the Diastereoisomers (1R,3S,5R,7R,8R,10S,13R) and (1R,3S,5S,7R,8R,10S,13R) in a Respective Ratio of 85:15 (Invention's Compound)

1) Preparation of 3-bromo-2-pentanone

A 1000 mL 3-neck round bottomed flask equipped with a magnetic stir bar and a reflux condenser was charged with 172 g of 2-pentanone, 30.4 g of KClO$_3$, 140 mL of water and heated to 50° C. Bromine (176 g) is then introduced into dropwise over a 2 h period causing the reaction to exotherm to 80° C. At the end of the introduction of bromide, the reaction mixture was stirred for an additional 40 min at 50° C. before cooling it to 18° C. in an ice/water bath. 10 g of MgO was introduced in portions maintaining the temperature of the reaction between 18-28° C. with the ice-water bath. The mixture was then filtered over celite, rinsed with ether and the aqueous phase extracted once with ether. After drying the organic extracts over Na$_2$SO$_4$ and concentrating it on the rotovap, 417 g of crude containing 59% of 3-bromo-2-pentanone and 29% of 1-bromo-2-pentanone. The two bromoketones were then separated by distillation using a 25 cm Wiedmer column to give 110 g of 95% pure 3-bromo-2-pentanone.

$^1$H-NMR (600 MHz, CDCl3): δ (ppm) 4.18 (d, d=J9, 6 Hz, 1H), 2.36 (s, 3H), 2.00 (m, 2H), 1.03 (t=J7 Hz, 3H) $^{13}$C (150 MHz, CDCl$_3$): δ (ppm) 11.9, 26.2, 27.0, 56.1, 76.8, 77.0, 77.2, 202.1

2) Preparation of 3-bromo-2,2-dimethoxypentane

A 250 mL 3-neck round bottomed flask equipped with a magnetic stir bar and a reflux condenser was charged with 41 g of 3-bromo-2-pentanone, 4.1 g of methanol and 0.3 g of pTSA. To this solution at 20° C., 27 g of trimethylorthoformate was added over a 70 min period causing the reaction temperature to rise to 26° C. during the addition. After 30 min at room temperature, the temperature was increased to 50° C. After 2.5 h another 2.73 g of trimethylorthoformate was added and the reaction continued at 50° C. for another 2 g then another 2.73 g of trimethylorthoformate along with 0.1 g of pTSA were added. After another 16 h of reaction time at 50° C., complete conversion of the starting material was observed. After cooling to room temperature, the reaction was quenched by pouring it into saturated NaHCO$_3$ and diluted with ether. After phase separation, the aqueous phase was extracted with ether and the combined organic extracts were washed once more with NaHCO$_3$, dried over Na$_2$SO$_4$ and concentrated on the rotovap to give 51.8 g of crude 3-bromo-2,2-dimethoxypentane at 93% purity. The latter was distilled with a vigreux column to give 47.5 g of 93% pure 3-bromo-2,2-dimethoxypentane.

$^1$H-NMR (600 MHz, CDCl3): δ (ppm) 3.93 (dd, J 1.8, 11.3 Hz, 1H), 3.22 (s, 6H), 1.99-2.06 (m, 1H), 1.57-1.66 (m, 1H), 1.39 (s, 3H), 1.09 (t, J 7.3 Hz, 3H) $^{13}$C (150 MHz, CDCl$_3$): δ (ppm) 13.2, 14.1, 16.6, 17.4, 27.4, 31.3, 34.2, 47.7, 48.4, 49.1, 60.3, 76.8, 77.0, 77.2, 102.0

3) Preparation of (E)-2,2-dimethoxy-3-pentene

A 100 mL 3-neck round bottomed flask equipped with a magnetic stir bar and a reflux condenser was charged with 7.6 g of 3-bromo-2,2-dimethoxypentane, 50 mL of DMSO and 7 g of solid potassium t-butoxide causing the reaction temperature to rise to 45° C. before subsiding. The reaction was stirred for an additional 15 min then quenched by pouring it into cold water and diluted with ether. After phase separation, the aqueous phase was extracted twice with ether, washed with water, brine, dried over Na$_2$SO$_4$ and concentrated on the rotovap to give 7.89 g of crude containing 91% of (E)-2,2-dimethoxy-3-pentene. Following bulb-to-bulb distillation, 4.24 g of 96% pure (E)-2,2-dimethoxy-3-pentene was obtained.

$^1$H-NMR (600 MHz, CDCl3): δ (ppm) 5.95-6.01 (m, 1H), 5.42 (dq, 1.7, 15.5 Hz, 1H), 3.11 (s, 6H), 1.55 (dd, 1.7, 6.6 Hz, 3H), 1.36 (s, 3H)
$^{13}$C (150 MHz, CDCl$_3$): δ (ppm) 17.6, 24.1, 48.5, 99.8, 127.5, 128.0, 128.2, 133.4

4) Preparation of 5,7,9,9,13-pentamethyl-5-[(1E)-1-propen-1-yl]-4,6-dioxatetracyclo[6.5.1.0$^{1,10}$.0$^{3,7}$] tetradecane in a Form of a Mixture Comprising the Diastereoisomers (1R,3S,5R,7R,8R,10S,13R) and (1R,3S,5S,7R,8R,10S,13R) in a Respective Ratio of 85:15

A 1 L 3-neck round bottomed flask equipped with a magnetic stir bar and a Dean-Stark trap was charged with 11 g of cedrenediol, 30 g of 2,2-dimethoxy-3-pentene, 0.26 g of pTSA and 550 mL of cyclohexane. The mixture was refluxed for 10 min, cooled to room temperature then quenched by pouring the reaction mixture into saturated NaHCO$_3$. The reaction mixture was extracted twice with ether, washed with water, dried over Na$_2$SO$_4$ and concentrated on the rotovap to give 23.2 g of crude containing 40% of a diastereomeric mixture of (1R,3S,5R,7R,8R,10S,13R)-5,7,9,9,13-pentamethyl-5-[(1E)-1-propen-1-yl]-4,6-dioxatetracyclo[6.5.1.01,10.03,7]tetradecane and (1R,3S,5S,7R,8R,10S,13R)-5,7,9,9,13-pentamethyl-5-[(1E)-1-propen-1-yl]-4,6-dioxatetracyclo[6.5.1.01,10.03,7]tetradecane ((1R,3S,5R,7R,8R,10S,13R)/(1R,3S,5S,7R,8R,10S,13R)=85/15). The crude was purified by silica column chromatography using a gradient of pentane/ether (from 9/1-6/4), which resulted in the isolation of 7 g of 93% 5,7,9,9,13-pentamethyl-5-[(1E)-1-propen-1-yl]-4,6-dioxatetracyclo[6.5.1.01,10.03,7]tetradecane ((1R,3S,5R,7R,8R,10S,13R)/(1R,3S,5S,7R,8R,10S,13R)=85/15).

$^1$H-NMR (600 MHz, CDCl3): δ (ppm) 5.73-5.8 (m, 1H), 5.68 (dq, J 1.5, 15.4 Hz, 1H), 4.07 (dd, J 6.7, 9 Hz, 1H), 2.03 (d, J 11.7 Hz, 1H), 1.92-1.99 (m, 2H), 1.49-1.88 (m, 14H), 1.38-1.48 (m, 5H), 1.29 (sextet J 6 Hz, 1H), 1.14 (s, 3H), 1.04 (s, 3H), 0.82 (d, J 7.2, 3H)

$^{13}$C (150 MHz, CDCl$_3$): δ (ppm) 15.4, 17.5, 25.4, 26.9, 28.7, 29.1, 31.0, 35.8, 38.5, 41.3, 41.9, 42.6, 52.6, 57.6, 58.3, 76.8, 77.0, 77.2, 78.6, 85.3, 107.5, 123.9, 136.7

Example 2

Synthesis of 5,7,9,9,13-pentamethyl-5-[(1E)-1-propen-1-yl]-4,6-dioxatetracyclo[6.5.1.0$^{1,10}$.0$^{3,7}$]tetradecane in a Form of a Mixture Comprising the Diastereoisomers (1R,3S,5R,7R,8R,10S,13R) and (1R,3S,5S,7R,8R,10S,13R) in a Respective Ratio of 2:98 (Invention's Compound)

1) Preparation of a Mixture of (2S,3aS,4aR,5R,7aS,9R,9aR)-2-((S)-1-bromopropyl)-2,5,8,8,9a-pentamethyloctahydro-4H-4a,9-methanoazuleno[5,6-d][1,3]dioxole and (2R,3aS,4aR,5R,7aS,9R,9aR)-2-((R)-1-bromopropyl)-2,5,8,8,9a-pentamethyloctahydro-4H-4a,9-methanoazuleno[5,6-d][1,3]dioxole A 500 mL 3-neck round bottomed flask equipped with a magnetic stir bar and a Dean-Stark trap was charged with 5 g of cedrenediol, 22 g of 3-bromo-2,2-dimethoxypentane (prepared in example 13)), 0.82 g of Al$_2$(SO$_4$)$_3$-18H$_2$O and 250 mL of cyclohexane. The mixture was refluxed for 39 h, then quenched by pouring the reaction mixture into saturated NaHCO$_3$. The reaction mixture was extracted twice with ether, washed with water, dried over Na$_2$SO$_4$ and concentrated on the rotovap to give 15.9 g of crude concentrate containing a diastereomeric mixture of (2S,3aS,4aR,5R,7aS,9R,9aR)-2-((S)-1-bromopropyl)-2,5,8,8,9a-pentamethyloctahydro-4H-4a,9-methanoazuleno[5,6-d][1,3]dioxole and (2R,3aS,4aR,5R,7aS,9R,9aR)-2-((R)-1-bromopropyl)-2,5,8,8,9a-pentamethyloctahydro-4H-4a,9-methanoazuleno[5,6-d][1,3]dioxole with (2S,3aS,4aR,5R,7aS,9R,9aR)-2-((S)-1-bromopropyl)-2,5,8,8,9a-pentamethyloctahydro-4H-4a,9-methanoazuleno[5,6-d][1,3]dioxole as the major stereoisomer. The crude was distilled on the kuegel-rohr in order to remove the light boiling components leaving behind 8.38 g of residue. The crude bromoketal was taken to the next step without further purification 2) Preparation of 5,7,9,9,13-pentamethyl-5-[(1E)-1-propen-1-yl]-4,6-dioxatetracyclo[6.5.1.0$^{1,10}$.0$^{3,7}$]tetradecane in a Form of a Mixture Comprising the Diastereoisomers (1R,3S,5R,7R,8R,10S,13R) and (1R,3S,5S,7R,8R,10S,13R) in a Respective Ratio of 2:98

A 100 mL 3-neck round bottomed flask equipped with a magnetic stir bar and reflux condenser was charged with 7.1 g of crude bromide obtained in the previous step (36%), 2.6 g of potassium t-butoxide, 50 mL of DMSO and heated to 80° C. for 30 min to complete conversion of the starting material. The reaction mixture was quenched by pouring it into 50 mL of water then diluted with 50 mL of ether and 100 mL of heptane. After separating the phases, the aqueous phase was extracted with heptane, washed three times with water, dried over Na$_2$SO$_4$ and concentrated on the rotovap to give 5.2 g of crude concentrate containing 41% of (1R,3S,5S,7R,8R,10S,13R)-5,7,9,9,13-pentamethyl-5-[(1E)-1-propen-1-yl]-4,6-dioxatetracyclo[6.5.1.01,10.03,7]tetradecane and 16% of (1R,3S,5R,7R,8R,10S,13R)-5,7,9,9,13-pentamethyl-5-[(1E)-1-propen-1-yl]-4,6-dioxatetracyclo[6.5.1.01,10.03,7]tetradecane. The crude was chromatographed on silica with a pentane/ether gradient (97/3 then 9/1) to obtain 0.68 g of 82% pure (1R,3S,5R,7R,8R,10S,13R)-5,7,9,9,13-pentamethyl-5-[(1E)-1-propen-1-yl]-4,6-dioxatetracyclo[6.5.1.01,10.03,7]tetradecane and 1.5 g of 95% pure (1R,3S,5S,7R,8R,10S,13R)-5,7,9,9,13-pentamethyl-5-[(1E)-1-propen-1-yl]-4,6-dioxatetracyclo[6.5.1.01,10.03,7]tetradecane.

$^1$H-NMR (600 MHz, CDCl3): δ (ppm) 5.73-5.8 (m, 1H), 5.71 (dq, J 1.4, 15.6 Hz, 1H), 4.07 (dd, J 8.1, 8.6 Hz, 1H), 2.03 (d, J 11.9 Hz, 1H), 1.96 (d, J 4.5 Hz, 1H), 1.64-1.86 (m, 7H), 1.48-1.63 (m, 9H), 1.36-1.47 (m, 2H), 1.26 (sextet J 6.2 Hz, 1H), 1.16 (s, 3H), 1.03 (s, 3H), 0.77 (d, J 7.1, 3H)

$^{13}$C (150 MHz, CDCl$_3$): δ (ppm) 15.3, 17.5, 25.6, 27.4, 28.8, 29.5, 30.9, 36.3, 38.5, 38.8, 42.1, 42.3, 52.5, 57.6, 58.6, 76.8, 77.0, 77.2, 79.0, 85.2, 107.4, 124.3, 136.7

Example 3

Synthesis of 5,7,9,9,13-pentamethyl-5-[(1E)-1-propen-1-yl]-4,6-dioxatetracyclo[6.5.1.0$^{1,10}$.0$^{3,7}$]tetradecane in a Form of a Mixture Comprising the Diastereoisomers (1R,3S,5R,7R,8R,10S,13R) and (1R,3S,5S,7R,8R,10S,13R) in a Respective Ratio of 98:2 (Invention's Compound)

The diastereoisomers mixture of (1R,3S,5R,7R,8R,10S,13R)-5,7,9,9,13-pentamethyl-5-[(1E)-1-propen-1-yl]-4,6-dioxatetracyclo[6.5.1.01,10.03,7]tetradecane (1R,3S,5S,7R,8R,10S,13R)-5,7,9,9,13-pentamethyl-5-[(1E)-1-propen-1-yl]-4,6-dioxatetracyclo[6.5.1.01,10.03,7]tetradecane in a respective ratio of 85/15 obtained in example 1 was further purified by silica column chromatography to provide (1R,3S,5R,7R,8R,10S,13R)-5,7,9,9,13-pentamethyl-5-[(1E)-1-propen-1-yl]-4,6-dioxatetradecane (1R,3S,5S,7R,8R,1S,13R)-5,7,9,9,13-pentamethyl-5-[(1E)-1-propen-1-yl]-4,6-dioxatetracyclo[6.5.1.01,10.03,7]tetradecane in a respective ratio of 98/2.

$^1$H-NMR (600 MHz, CDCl3): δ (ppm) 5.73-5.8 (m, 1H), 5.68 (dq, J 1.5, 15.4 Hz, 1H), 4.07 (dd, J 6.7, 9 Hz, 1H), 2.03 (d, J 11.7 Hz, 1H), 1.92-1.99 (m, 2H), 1.49-1.88 (m, 14H), 1.38-1.48 (m, 5H), 1.29 (sextet J 6 Hz, 1H), 1.14 (s, 3H), 1.04 (s, 3H), 0.82 (d, J 7.2, 3H)

$^{13}$C (150 MHz, CDCl$_3$): δ (ppm) 15.4, 17.5, 25.4, 26.9, 28.7, 29.1, 31.0, 35.8, 38.5, 41.3, 41.9, 42.6, 52.6, 57.6, 58.3, 76.8, 77.0, 77.2, 78.6, 85.3, 107.5, 123.9, 136.7

Example 4

Synthesis of (1R,3S,5R,7R,8R,10S,13R)-5,7,9,9,13-pentamethyl-5-[1-propyn-1-yl]-4,6-dioxatetracyclo[6.5.1.0$^{1,10}$.0$^{3,7}$]tetradecane (Invention's Compound)

1) Preparation of 4,4-dimethoxypent-2-yne

A 100 mL 3-neck round bottomed flask equipped with a magnetic stir bar and a reflux condenser under N$_2$ atmosphere was charged with 14.5 g of pent-3-yn-2-one (prepared according to a published procedure (P. Martin, M. Mueller, D. Flubacher, A. Boudier, H.-U. Blaser and D. Spielvogel Org. Proc. Res. & Dev. 2010, 14, 799-804), 5.7 g of methanol, 0.18 g of pTSA and finally 20.6 g of trimethylorthoformate over a 1 h period. The reaction mixture was heated to 50° C. and stirring continued for another 30 min then quenched by pouring it into NaHCO$_3$ then diluted with ether. The aqueous phase was extracted with ether and the combined extracts were washed with NaHCO$_3$, dried over Na$_2$SO$_4$ and concentrated on the rotovap to give 41 g of crude 4,4-dimethoxypent-2-yne at 71% purity. The latter was distilled using a 15 cm Wiedmer column to give 15.6 g of 92% pure 4,4-dimethoxypent-2-yne.

$^1$H-NMR (600 MHz, CDCl3): δ (ppm) 3.29 (s, 6H), 1.88 (s, 3H), 1.57 (s, 3H)

$^{13}$C (150 MHz, CDCl$_3$): δ (ppm) 3.4, 25.2, 49.9, 51.3, 76.9, 77.1, 77.27. 77.29, 80.8, 96.4

2) Preparation of (1R,3S,5R,7R,8R,10S,13R)-5,7,9,9,13-pentamethyl-5-[1-propyn-1-yl]-4,6-dioxatetracyclo[6.5.1.0$^{1,10}$.0$^{3,7}$]tetradecane A 250 mL 3-neck round bottomed flask equipped with a magnetic stir bar and a Dean-Stark trap was charged with 2 g of cedrenediol, 3.2 g of 4,4-dimethoxypent-2-yne, 0.33 g of Al$_2$(SO$_4$)$_3$-18H$_2$O, 100 mL of cyclohexane and heated to reflux for 16 h then quenched by pouring it into saturated Na$_2$CO$_3$ and diluted with ether. After phase separation, the organic phase was washed with 10% NaK tartrate, dried over Na$_2$SO$_4$ and concentrated on the rotovap to give 3.2 g of crude. The latter was purified by silica column chromatography using pentane/ether (97/3) to give 0.7 g of 5,7,9,9,13-pentamethyl-5-[1-propyn-1-yl]-4,6-dioxatetracyclo[6.5.1.0$^{1,10}$.0$^{3,7}$]tetradecane. Following bulb-to-bulb distillation, 0.7 g of 97% pure 5,7,9,9,13-pentamethyl-5-[1-propyn-1-yl]-4,6-dioxatetracyclo[6.5.1.0$^{1,10}$.0$^{3,7}$]tetradecane which crystallized upon standing.

$^1$H-NMR (600 MHz, CDCl3): δ (ppm) 4.05 (dd, J 7.2, 9 Hz, 1H), 2.72 (dd, J 7.2, 13.6 Hz, 1H), 2.6 (d, J 11.9 Hz, 1H), 2.01 (d, J 4.6 Hz, 1H), 1.92 (s, 3H), 1.69-1.82 (m, 3H), 1.5-1.54 (m, 1H), 1.46 (d, J 4.3, 6H), 1.17-1.43 (m, 4H), 0.95 (s, 3H), 0.88-0.92 (m, 6H)

$^{13}$C (150 MHz, CDCl$_3$): δ (ppm) 128.19, 128.10, 128.0, 127.95, 127.87, 101.06, 85.74, 83.01, 80.17, 79.81, 59.08, 58.13, 52.28, 42.75, 41.93, 39.34, 38.39, 36.94, 31.91, 30.79, 28.83, 28.05, 25.98, 15.67, 3.076

Example 5

Synthesis of (1R,3S,5R,7R,8R,10S,13R)-5,7,9,9,13-pentamethyl-5-[(1Z)-1-propen-1-yl]-4,6-dioxatetracyclo[6.5.1.0$^{1,10}$.0$^{3,7}$]tetradecane (Invention's Compound)

0.5 g of compound obtained in example 4 was hydrogenated with 53 mg of Lindlar's catalyst in ethanol (50 mL) at room temperature and 1 bar of H$_2$. The reaction mixture was filtered and concentrated to give 0.47 g of (1R,3S,5R,7R,8R,10S,13R)-5,7,9,9,13-pentamethyl-5-[(1 Z)-1-propen-1-yl]-4,6-dioxatetracyclo[6.5.1.0$^{1,10}$.0$^{3,7}$]tetradecane at 89% purity. The latter was chromatographed on silica (pentane/ether, 95/5) to give 0.36 g of 97% pure cis-ketal (1R,3S,5R,7R,8R,10S,13R)-5,7,9,9,13-pentamethyl-5-[(1Z)-1-propen-1-yl]-4,6-dioxatetracyclo[6.5.1.0$^{1,10}$ 0.0$^{3,7}$]tetradecane. Following distillation on the kuegel-rohr, 0.35 g of 97% (1R,3S,5R,7R,8R,10S,13R)-5,7,9,9,13-pentamethyl-5-[(1Z)-1-propen-1-yl]-4,6-dioxatetracyclo[6.5.1.0$^{1,10}$.0$^{3,7}$]tetradecane was obtained.

$^1$H-NMR (600 MHz, CDCl3): δ (ppm) 5.7 (dq, J 1.5, 11.8 Hz, 1H), 5.36-5.43 (m, 1H), 4.07 (t, J 8.1 Hz, 1H), 1.9-1.96 (m, 2H), 1.38-1.85 (m, 18H), 1.49-1.88 (m, 14H), 1.26 (sextet J 6 Hz, 1H), 1.14 (s, 3H), 1.03 (s, 3H), 0.77 (d, J 7 Hz, 3H)

$^{13}$C (150 MHz, CDCl$_3$): δ (ppm) 14.1, 15.3, 25.5, 27.5, 28.7, 29.3, 30.9, 36.1, 38.1, 38.7, 41.9, 42.3, 52.3, 57.4, 58.2, 76.8, 77.0, 77.2, 79.2, 84.5, 108.1, 124.0, 137.1

Example 6

Synthesis of (1R,3S,5R,7R,8R,10S,13R)-5-cyclopropyl-5,7,9,9,13-pentamethyl-4,6-dioxatetracyclo[6.5.1.0$^{1,10}$.0$^{3,7}$]tetradecane (Comparative Compound)

A 100 mL 3-neck round bottomed flask equipped with a magnetic stir bar and a reflux condenser was charged with 5 g of cedrenediol, 8.8 g of cyclopropylmethyl ketone, 2.5 g of trimethylorthoformate, 80 mL of cyclohexane and cooled to 0° C. The slurry was then charged with 0.08 g of TMSOTf and stirred at 0° C. for 2 h and 1 h at room temperature to partial conversion, then quenched by pouring the reaction mixture into saturated NaHCO$_3$ and diluted with ether. After phase separation, the aqueous phase was extracted twice with ether, washed with water, dried over Na$_2$SO$_4$ and concentrated on the rotovap to give 5.22 g of crude which solidified upon standing. The solid was recrystallized in hexane/EtOAc (9/1) giving 1.7 g of pure cedrenediol crystals (contaminated with 8% of (1R,3S,5R,7R,8R,10S,13R)-5-cyclopropyl-5,7,9,9,13-pentamethyl-4,6-dioxatetracyclo[6.5.1.0$^{1,10}$.0$^{3,7}$]tetradecane) and 3.3 g of mother liquour containing 33% of ketal (1R,3S,5R,7R,8R,10S,13R)-5-cyclopropyl-5,7,9,9,13-pentamethyl-4,6-dioxatetracyclo[6.5.1.0$^{1,10}$.0$^{3,7}$]tetradecane. The latter was purified by silica column chromatography using pentane/ether (95/5) to give 1.1 g of 93% pure (1R,3S,5R,7R,8R,10S,13R)-5-cyclopropyl-5,7,9,9,13-pentamethyl-4,6-dioxatetracyclo[6.5.1.0$^{1,10}$.0$^{3,7}$]tetradecane and 6% of cedranone. The material was re-chromatographed on silica a second time to give 0.7 g of 97% pure (1R,3S,5R,7R,8R,10S,13R)-5-cyclopropyl-5,7,9,9,13-pentamethyl-4,6-dioxatetracyclo[6.5.1.0$^{1,10}$.0$^{3,7}$]tetradecane.

$^1$H-NMR (600 MHz, CDCl3): δ (ppm) 4.05 (dd, J 6.6, 9 Hz, 1H), 1.91-2.01 (m, 3H), 1.75 (sextet, J 6.9 Hz, 1H), 1.49-1.66 (m, 8H), 1.41-1.48 (m, 4H), 1.29 (sextet, J 6 Hz, 1H), 1.13-1.21 (m, 4H), 1.04 (s, 3H), 0.81 (d, J 7.1H)

$^{13}$C (150 MHz, CDCl$_3$): δ (ppm) 3.1, 3.5, 15.4, 21.9, 25.4, 26.6, 28.5, 28.7, 31.1, 35.8, 38.5, 41.6, 41.9, 42.4, 52.3, 57.9, 58.6, 76.8, 77.0, 77.2, 79.3, 84.5, 109.7

Example 7

Synthesis of 5,7,9,9,13-pentamethyl-5-[2-methylcyclopropyl]-4,6-dioxatetracyclo[6.5.1.0$^{1,10}$.0$^{3,7}$]tetradecane in a Form of a Mixture Comprising the Diastereoisomers (1R,3S,5R,7R,8R,10S,13R) and (1R,3S,5S,7R,8R,10S,13R) in a Respective Ratio of 91:9 (Comparative Compounds)

1) Preparation of 1-(2-methylcyclopropyl)ethan-1-one

A 1500 mL reaction flask equipped with a mechanical stirrer was placed under N2 atmosphere and charged with 26 g of 60% NaH followed by 300 mL of DMSO. The slurry was cooled to 0° C. then introduced with trimethylsulfoxonium iodide in portions during a 1 h period. 3-penten-2-one (70% pure, rest being mesityloxide) was then added over a 30 min period causing the temperature to rise to 20° C. The reaction was stirred for an additional 3 h to complete conversion of the starting ketone then quenched by adding saturated NH$_4$Cl followed by dilution with 200 mL of ether. The aqueous phase was extracted with ether and the combined organic extracts were washed sequentially with saturated NH$_4$Cl, 10% Na$_2$SO$_3$, NaHCO$_3$ and brine. After drying with Na$_2$SO$_4$ and concentrating the reaction mixture on the rotovap at atmospheric pressure, 85 g of crude was obtained which was fractionated on a 15 cm Wiedmer column to give 25.5 g of cyclopropanated ketone 1-(2-methylcyclopropyl) ethan-1-one at 64% purity along with 31 g of ether and 29 g of pot residue. Ketone 1-(2-methylcyclopropyl)ethan-1-one was used without further purification.

2) Preparation of 1-(1,1-dimethoxyethyl)-2-methylcyclopropane

At 25° C., a 250 mL 3-neck round bottomed flask equipped with a magnetic stir bar and a reflux condenser was charged with 20 g of 64% pure 1-(2-methylcyclopropyl) ethan-1-one, 63 g of methanol, 0.015 g of p-toluenesulfonic acid and 21 g of trimethylorthoformate, causing the reaction temperature to increase to 34° C. After 50 min at room temperature, the reaction was quenched by pouring it into saturated NaHCO$_3$ and diluted with ether. After phase separation, the aqueous phase was extracted with ether and the combined organic extracts were washed once more with NaHCO$_3$, dried over Na$_2$SO$_4$ and concentrated on the rotovap to give 44 g of crude 1-(1,1-dimethoxyethyl)-2-methylcyclopropane at 32% purity. The latter was distilled on a 15 cm Wiedmer column leading to decomposition of the desired product. Distilled fractions containing 15-21% of ketal 1-(1,1-dimethoxyethyl)-2-methylcyclopropane were combined (8.6 g) and chromatographed on silica with pentane/ether (97/2) to give 2 g of 80% pure ketal 1-(1,1-dimethoxyethyl)-2-methylcyclopropane.

$^1$H-NMR (600 MHz, CDCl3): δ (ppm) 3.12 (s, 3H), 3.09 (s, 3H), 1.31 (s, 3H), 0.99-1.07 (m, 1H), 0.94 (d, J 6 Hz, 3H), 0.74-0-78 (m, 1H), 0.47-0.52 (m, 1H), 0.06-0.11 (m, 1H)

$^{13}$C (150 MHz, C$_6$D$_6$): δ (ppm) 9.0, 9.9, 18.3, 23.3, 27.0, 48.1, 48.3, 127.8, 128.0, 128.2

3) Preparation of 5,7,9,9,13-pentamethyl-5-[2-methylcyclopropyl]-4,6-dioxatetracyclo[6.5.1.0$^{1,10}$.0$^{3,7}$] tetradecane in a Form of a Mixture Comprising the Diastereoisomers (1R,3S,5R,7R,8R,10S,13R) and (1R,3S,5S,7R,8R,10S,13R) in a Respective Ratio of 91:9

A 100 mL 3-neck round bottomed flask equipped with a magnetic stir bar and a Dean-Stark trap was charged with 1.25 g of cedrenediol, 1.93 g of 80% pure 1-(1,1-dimethoxyethyl)-2-methylcyclopropane, 0.03 g of p-toluenesulfonic acid, 70 mL of cyclohexane and refluxed for 45 min then quenched by pouring the reaction mixture into saturated NaHCO$_3$ and diluted with ether. After phase separation, the aqueous phase was extracted twice with ether, washed with water, dried over Na$_2$SO$_4$ and concentrated on the rotovap to give 1.81 g of crude 5,7,9,9,13-pentamethyl-5-[2-methylcyclopropyl]-4,6-dioxatetracyclo[6.5.1.0$^{1,10}$.0$^{3,7}$]tetradecane at 47%. The latter was purified by silica column chromatography using hexane/EtOAc (95/5) to then distilled on the kuegel-rohr to give 0.93 g of 94% pure 5,7,9,9,13-pentamethyl-5-[2-methylcyclopropyl]-4,6-dioxatetracyclo[6.5.1.0$^{1,10}$.0$^{3,7}$]tetradecane in a form of a mixture comprising the diastereoisomers (1R,3S,5R,7R,8R,10S,13R) and (1R,3S,5S,7R,8R,10S,13R) in a respective ratio of 91:9 (R/S=91/9).

$^1$H-NMR (600 MHz, CDCl3): δ (ppm) 3.89-3.94 (m, 1H), 2.25 (d, J 11.9, 1H), 2.02 (t, J 4 Hz, 1H), 1.81-1.87 (m, 1H), 1.70-1.79 (m, 3H), 1.6-1.67 (m, 7H), 1.23-1.49 (m, 5H), 1.15-1.22 (m, 1H), 0.97-1.06 (m, 8H), 0.91 (s, 3H), 0.77 (dd, J 1.9, 7 Hz, 3H)

$^{13}$C (150 MHz, CDCl$_3$): δ (ppm) 11.68, 11.69, 15.605, 15.612, 18.4, 18.9, 25.6, 28.2, 28.8, 31.131, 31.139, 36.2, 39.09, 39.10, 42.16, 42.225, 42.234, 42.24, 58.4, 58.7, 127.87, 127.95, 128.03, 128.1, 128.2, 128.30, 128.32, 128.5, 133.4

Example 8

Synthesis of 7,9,9,13-tetramethyl-5-(2-methyl-1-propen-1-yl)-4,6-dioxatetracyclo[6.5.1.0$^{1,10}$.0$^{3,7}$] tetradecane in a Form of a Mixture Comprising the Diastereoisomers (1R,3S,5R,7R,8R,10S,13R) and (1R,3S,5S,7R,8R,10S,13R) in a Respective Ratio of 12:88 (Comparative Compound)

A 50 mL 3-neck round bottomed flask equipped with a magnetic stir bar and reflux condenser was charged with 2 g of cedrenediol, 7 g of 3-methyl-but-2-enal, 0.04 g of oxalic acid and 20 mL of cyclopentane. The mixture was allowed to stir at room temperature for 4 days to 80% conversion of the starting material. The reaction mixture was extracted twice with ether, washed twice with dilute aqueous NaOH, dried over Na$_2$SO$_4$ and concentrated on the rotovap to give 2.68 g of crude concentrate. The crude was chromatographed on silica starting first with 99/1 pentane/ether then gradually increasing the polarity of the eluting solvent to give after bulb-to-bulb distillation 1.8 g of 91% pure 7,9,9,13-tetramethyl-5-(2-methyl-1-propen-1-yl)-4,6-dioxatetracyclo[6.5.1.0$^{1,10}$.0$^{3,7}$]tetradecan as a 88/12 mixture of diastereomers (1R,3S,5S,7R,8R,10S,13R)-7,9,9,13-tetramethyl-5-(2-methyl-1-propen-1-yl)-4,6-dioxatetracyclo[6.5.1.0$^{1,10}$.0$^{3,7}$]tetradecane and (1R,3S,5R,7R,8R,10S,13R)-7,9,9,13-tetramethyl-5-(2-methyl-1-propen-1-yl)-4,6-dioxatetracyclo[6.5.1.0$^{1,10}$.0$^{3,7}$]tetradecane.

$^1$H-NMR (600 MHz, CDCl$_3$): δ (ppm) 0.85 (d, J 7.1 Hz, 3H), 1.03 (s, 3H), 1.14 (s, 3H), 1.23-1.36 (m, 1H), 1.42 (s, 3H), 1.43-1.69 (m, 4H), 1.67 (t, J 7.3 Hz, 1H), 1.77 (s, 3H), 1.78 (s, 3H), 1.82-1.93 (m, 3H), 1.94 (d, J 4.6 Hz, 1H), 4.11 (t, J8.1 Hz, 1H), 5.3 (d, J 7.9 Hz, 1H), 5.81 (d, J 7.8 Hz, 1H)

$^{13}$C (150 MHz, CDCl$_3$): δ (ppm) 15.5, 18.2, 25.4, 27.9, 28.4, 30.7, 36.0, 37.2, 39.1, 41.7, 42.4, 52.2, 57.7, 58.0, 76.8, 77.0, 77.2, 78.4, 83.4, 97.5, 123.7

Example 9

Synthesis of 7,9,9,13-tetramethyl-5-(1-propen-1-yl)-4,6-dioxatetracyclo[6.5.1.0$^{1,10}$.0$^{3,7}$]tetradecane in a Form of a Mixture Comprising the Diastereoisomers (1R,3S,5R,7R,8R,10S,13R) and (1R,3S,5S,7R, 8R,10S,13R) in a Respective Ratio of 8:92 or 41:59 (Comparative Compound)

A 50 mL 3-neck round bottomed flask equipped with a magnetic stir bar and reflux condenser was charged with 2 g of cedrenediol, 6 g of crotonaldehyde, 0.04 g of oxalic acid and 20 mL of cyclopentane. The mixture was allowed to stir at room temperature for 5 days then quenched with dilute aqueous NaOH. The reaction mixture was extracted twice with ether, washed twice with water, dried over Na$_2$SO$_4$ and concentrated on the rotovap to give 2.27 g of crude concentrate. The crude was chromatographed on silica with 9/1 cyclohexane/ethyl acetate and the purified fractions distilled on the kuegel-rohr to give 0.79 g of 85% pure 7,9,9,13-tetramethyl-5-(1-propen-1-yl)-4,6-dioxatetracyclo[6.5.1.0$^{1,10}$.0$^{3,7}$]tetradecane as a 92/8 mixture of diastereoisomers (1R,3S,5S,7R,8R,10S,13R) and (1R,3S,5R,7R,8R,10S,13R) and 0.71 g of 100% pure 7,9,9,13-tetramethyl-5-(1-propen-1-yl)-4,6-dioxatetracyclo[6.5.1.0$^{1,10}$.0$^{3,7}$]tetradecane as a 59/41 mixture of diastereoisomers (1R,3S,5S,7R,8R,10S,13R) and (1R,3S,5R,7R,8R,10S,13R).

RMN of 92/8 mixture of diastereoisomers (1R,3S,5S,7R,8R,10S,13R) and (1R,3S,5R,7R,8R,10S,13R)

$^1$H-NMR (600 MHz, CDCl$_3$): δ (ppm) 0.84 (d, J 7.1 Hz, 3H), 1.02 (s, 3H), 1.14 (s, 3H), 1.28-1.36 (m, 1H), 1.39-1.49 (m, 4H), 1.5-1.61 (m, 3H), 1.66 (t, J 7.3 Hz, 1H), 1.70-1.80 (m, 4H), 1.82-1.93 (m, 3H), 1.94 (d, J 4.6 Hz, 1H), 4.11 (t, J8.1 Hz, 1H), 5.44 (d, J 7.2 Hz, 1H), 5.54-5.59 (m, 1H), 5.87-5.89 (m, 1H)

$^{13}$C (150 MHz, CDCl$_3$): δ (ppm) 15.4, 17.6, 25.5, 26.9, 27.7, 28.5, 30.7, 36.1, 37.1, 39.1, 41.8, 42.3, 52.1, 57.7, 58.1, 76.8, 77.0, 77.2, 78.4, 83.6, 102.0, 129.9, 132.3

Example 10

Synthesis of 7,9,9,13-tetramethyl-5-(3-buten-1-yl)-4,6-dioxatetracyclo[6.5.1.0$^{1,10}$.0$^{3,7}$]tetradecane in a Form of a Mixture Comprising the Diastereoisomers (1R,3S,5R,7R,8R,10S,13R) and (1R,3S,5S,7R, 8R,10S,13R) in a Respective Ratio of 9:91 (Comparative Compound)

A 50 mL 3-neck round bottomed flask equipped with a magnetic stir bar and reflux condenser was charged with 1 g of cedrenediol, 3.5 g of 4-pentenal, 0.02 g of oxalic acid and 10 mL of cyclopentane. The mixture was allowed to stir at room temperature for 4 days to 25% conversion, and then quenched with dilute aqueous NaOH. The reaction mixture was extracted twice with ether, washed twice with water, dried over Na$_2$SO$_4$ and concentrated on the rotovap to give 1.76 g of crude concentrate. The crude was chromatographed on silica with 9/1 cyclohexane/ethyl acetate then distilled on the kuegel-rohr to give 0.23 g of 97% pure 7,9,9,13-tetramethyl-5-(3-buten-1-yl)-4,6-dioxatetracyclo[6.5.1.0$^{1,10}$.0$^{3,7}$]tetradecane as a 91/9 mixture of diastereomers (1R,3S,5S,7R,8R,10S,13R) and (1R,3S,5R,7R,8R,10S,13R).

$^1$H-NMR (600 MHz, CDCl$_3$): δ (ppm) 0.81 (d, J 7.2 Hz, 3H), 1.02 (s, 3H), 1.16 (s, 3H), 1.24-1.33 (m, 1H), 1.38 (s, 3H), 1.40-1.49 (m, 1H), 1.5-1.69 (m, 3H), 1.7-1.89 (m, 5H), 1.91-1.99 (m, 2H), 2.03 (d, J 4.6 Hz, 1H), 2.17-2.24 (m, 2H), 3.91 (t, J 7.8 Hz, 1H), 4.95-5.00 (m, 1H), 5.03-5.09 (m, 1H), 5.14 (t, J 5.4 Hz, 1H), 5.83-5.91 (m, 1H)

$^{13}$C (150 MHz, CDCl$_3$): δ (ppm) 15.4, 23.2, 25.3, 28.5, 29.1, 30.6, 35.77, 35.84, 36.1, 38.2, 41.65, 41.78, 42.8, 53.0, 57.2, 57.5, 76.8, 77.0, 77.2, 78.4, 84.0, 102.1, 114.7, 138.1

Example 11

Synthesis of 5-(3-buten-1-yl)-5,7,9,9,13-pentamethyl-4,6-dioxatetracyclo[6.5.1.0$^{1,10}$.0$^{3,7}$]tetradecane in a Form of a Mixture Comprising the Diastereoisomers (1R,3S,5R,7R,8R,10S,13R) and (1R,3S,5S, 7R,8R,10S,13R) in a Respective Ratio of 82:18 (Comparative Compound)

A 100 mL 3-neck round bottomed flask equipped with a magnetic stir bar and a Dean-Stark trap was charged with 1 g of cedrenediol, 2 g of 5-penten-2-one, 0.038 g of pTSA and 50 mL of cyclohexane. The reaction was refluxed for 17 h to complete conversion of the starting material, cooled to room temperature then quenched by pouring the reaction mixture into saturated NaHCO$_3$. After phase separation, the aqueous phase was extracted twice with ether, washed with water, dried over Na$_2$SO$_4$ and concentrated on the rotovap to give 1.1 g of crude containing 45% of a diastereomeric mixture of (1R,3S,5R,7R,8R,10S,13R)-5-(3-buten-1-yl)-5,7,9,9,13-pentamethyl-4,6-dioxatetracyclo[6.5.1.0$^{1,10}$.0$^{3,7}$]tetradecane and (1R,3S,5S,7R,8R,10S,13R)-5-(3-buten-1-yl)-5,7,9,9,13-pentamethyl-4,6-dioxatetracyclo[6.5.1.0$^{1,10}$.0$^{3,7}$]tetradecane in a respective ratio of 82/18. The crude was purified by silica column chromatography using a gradient of pentane/ether (from 95/5-9/1), to give 0.5 g of 96% pure (1R,3S,5R,7R,8R,10 S,13R)-5-(3-buten-1-yl)-5,7,9,9,13-pentamethyl-4,6-dioxatetracyclo[6.5.1.0$^{1,10}$.0$^{3,7}$]tetradecane and (1R,3S,5S,7R,8R,10S,13R)-5-(3-buten-1-yl)-5,7,9,9,13-pentamethyl-4,6-dioxatetracyclo[6.5.1.0$^{1,10}$.0$^{3,7}$]tetradecane in a respective ratio of 82/18.

$^1$H-NMR (600 MHz, CDCl3): δ (ppm) 0.82 (d, J 7 Hz, 3H), 1.04 (s, 3H), 1.16 (s, 3H), 1.33-1.25 (m, 1H), 1.38-2.02 (m, 20H), 2.19 (q, J 9 Hz, 2H), 4.06 (dd, J 7 Hz, 10 Hz, 1H), 4.94 (dd, J 1 Hz, 10 Hz, 1H), 5.02 (dd, J 1 Hz, 18 Hz, 1H), 5.8-5.9 (m, 1H)

$^{13}$C (150 MHz, CDCl$_3$): δ (ppm) 15.4, 25.4, 26.7, 27.8, 28.7, 29.5, 31.2, 35.8, 38.5, 41.2, 41.9, 42.5, 42.6, 52.4, 57.4, 58.7, 76.8, 77.0, 77.2, 78.6, 85.0, 110.3, 114.1, 138.60, 138.61

Example 12

Synthesis of 7',9',9',13'-tetramethyl-4',6'-dioxaspiro[cyclohexane-1,5'-tetracyclo[6.5.1.0$^{1,10}$.0$^{3,7}$]tetradecane]-2-ene in a Form of a Mixture Comprising the Diastereoisomers (1R,1'R,3'S,7'R,8'R,10'S,13'R) and (1S,1'R,3'S,7'R,8'R,10'S,13'R) in a Respective Ratio of 59:41 (Comparative Compound)

A 100 mL 3-neck round bottomed flask equipped with a magnetic stir bar and a Dean-Stark trap was charged with 1 g of cedrenediol, 3 g of 3,3-dimethoxycyclohex-1-ene, 0.03 g of pTSA and 50 mL of cyclohexane. The reaction was refluxed for 2 h to complete conversion of the starting material, cooled to room temperature then quenched by pouring it into saturated NaHCO$_3$. After phase separation, the aqueous phase was extracted twice with ether, washed with water, dried over Na$_2$SO$_4$ and concentrated on the rotovap to give 3.2 g of crude containing 39% of a diastereomeric mixture of (1R,1'R,3'S,7'R,8'R,10'S,13'R)-7',9',9', 13'-tetramethyl-4',6'-dioxaspiro[cyclohexane-1,5'-tetracyclo[6.5.1.0$^{1,10}$.0$^{3,7}$]tetradecane]-2-ene and (1R,1'R,3'S,7'R,8'R,10'S,13'R)-7',9',9',13'-tetramethyl-4',6'-dioxaspiro[cyclohexane-1,5'-tetracyclo[6.5.1.0$^{1,10}$.0$^{3,7}$]tetradecane]-2-ene in a respective molar ratio of 59/41. The crude was purified by silica column chromatography using a gradient of pentane/ether (from 95/5-9/1), to give 0.81 g of 84% 7',9',9',13'-tetramethyl-4',6'-dioxaspiro[cyclohexane-1,5'-tetracyclo[6.5.1.0$^{1,10}$.0$^{3,7}$]tetradecane]-2-ene which after careful bulb-to-bulb distillation gave 0.64 g of 95% pure 7',9',9',13'-tetramethyl-4',6'-dioxaspiro[cyclohexane-1,5'-tetracyclo[6.5.1.0$^{1,10}$.0$^{3,7}$]tetradecane]-2-ene as a 60/40 mixture of diastereomers (1R,1'R,3'S,7'R,8'R,10'S,13'R) and (1S,1'R,3'S,7'R,8'R,10'S, 13'R).

$^1$H-NMR (600 MHz, CDCl3): δ (ppm) 5.83-5.95 (m, 3H), 5.77 (d, J 10 Hz, 1H), 4.09 (dd, J 7 Hz, 9 Hz, 2H), 1.37-2.1 (m, 36H), 1.36-1.24 (m, 2H), 1.6 (s, 6H), 1.04 (s, 6H), 0.82 (d, 6H)

$^{13}$C (150 MHz, CDCl$_3$): δ (ppm) 15.5, 20.67, 20.72, 24.5, 24.6, 25.39, 25.40, 27.82, 27.89, 28.69, 28.71, 31.07, 31.10, 35.83, 35.85, 37.04, 37.59, 38.55, 38.63, 41.45, 41.68, 41.85, 41.91, 42.51, 42.54, 52.42, 52.52, 57.20, 57.27, 58.35, 58.44, 76.8, 77.0, 77.2, 78.5, 78.7, 84.91, 84.96, 106.3, 131.1, 131.7, 132.1, 132.3

Example 13

Synthesis of 7',9',9',13'-tetramethyl-4',6'-dioxaspiro[cyclopentane-1,5'-tetracyclo[6.5.1.0$^{1,10}$.0$^{3,7}$]tetradecane]-2-ene a Form of a Mixture Comprising the Diastereoisomers (1S,1'R,3'S,7'R,8'R,10'S,13'R) and (1R,1'R,3'S,7'R,8'R,10'S,13'R) in a Respective Ratio of 32:68 (Comparative Compound)

A 250 mL 3-neck round bottomed flask equipped with a magnetic stir bar and a reflux condenser was charged with 1.9 g of cedrenediol, 5 g of 3,3-dimethoxycyclopent-1-ene, 0.16 g of Al$_2$(SO$_4$)$_3$·18H$_2$O and 150 mL of cyclohexane. The reaction was heated at 50° C. for 21 h then quenched by pouring it into saturated NaHCO$_3$. After phase separation, the aqueous phase was extracted twice with ether, washed with water, dried over Na$_2$SO$_4$ and concentrated on the rotovap to give 6.6 g of crude. The crude was purified by two successive silica column chromatographies using pentane/ether (first separation 9/1, second separation 95/5 to 9/1), to ultimately give 0.81 g of 72% 5,7,9,9,13-pentamethyl-5-vinyl-4,6-dioxatetracyclo[6.5.1.0$^{1,10}$.0$^{3,7}$]tetradecane in a form of a mixture comprising the diastereoisomers (1R,3S, 5R,7R,8R,10S,13R) and (1R,3S,5S,7R,8R,10S,13R) in a respective ratio of 68:32 which after careful bulb-to-bulb distillation led to 0.51 g of 94% pure 5,7,9,9,13-pentamethyl-5-vinyl-4,6-dioxatetracyclo[6.5.1.0$^{1,10}$.0$^{3,7}$]tetradecane in a form of a mixture comprising the diastereoisomers (1R,3S,5R,7R,8R,10S,13R) and (1R,3S,5S,7R,8R,10S,13R) in a respective ratio of 68:32.

$^1$H-NMR (600 MHz, CDCl3): δ (ppm) 6.06-6.11 (m, 1H), 5.83-5.85 (m, 0.54H), 5.78-5.81 (m, 0.44H), 4.03-4.09 (m, 1H), 2.34-2.42 (m, 2H), 2.18-2.26 (m, 2H), 1.81-2.03 (m, 4H), 1.71-1.79 (m, 1H), 1.65 (t, J 8 Hz, 1H), 1.38-1.6 (m, 8H), 1.25-1.35 (m, 1H), 1.16 (s, 2H), 1.15 (s, 1H), 1.04 (s, 2H), 1.03 (s, 1H), 0.84 (d, J 3 Hz, 2H), 0.83 (d, J3 Hz, 2H)

$^{13}$C (150 MHz, CDCl$_3$): δ (ppm) 15.4, 25.41, 25.43, 25.92, 26.1, 28.61, 28.64, 29.4, 29.7, 30.6, 30.7, 35.98, 35.99, 37.7, 37.9, 38.7, 38.8, 39.3, 40.3, 41.8, 42.48, 42.52, 52.48, 52.57, 56.92, 57.01, 57.7, 57.9, 76.8, 77.0, 77.2, 78.32, 78.35, 84.37, 84.48, 119.6, 119.7, 133.1, 133.5, 136.7, 136.8

Example 14

Synthesis of 5-ethyl-7,9,9,13-tetramethyl-5-vinyl-4,6-dioxatetracyclo[6.5.1.0$^{1,10}$.0$^{3,7}$]tetradecane in a Form of a Mixture Comprising the Diastereoisomers (1R,3S,5R,7R,8R,10S,13R) and (1R,3S,5S,7R,8R,10S,13R) in a Respective Ratio of 59:41 (Comparative Compound)

A 250 mL 3-neck round bottomed flask equipped with a magnetic stir bar and a Dean-Stark trap was charged with 3 g of cedrenediol, 8 g of 2-ethyl-2-vinyl-1,3-dioxolane, 0.072 g of pTSA and 150 mL of cyclohexane. The reaction was refluxed for 24 h, cooled to room temperature then quenched by pouring it into saturated NaHCO$_3$. After phase separation, the aqueous phase was extracted twice with ether, washed with water, dried over Na$_2$SO$_4$ and concentrated on the rotovap to give 5.15 g of crude. The latter was purified by 2 successive silica column chromatographies using pentane/ether (first chromatography 95/5, second chromatography 97/3), to give 0.6 g of 96% pure 5-ethyl-7,9,9,13-tetramethyl-5-vinyl-4,6-dioxatetracyclo[6.5.1.0$^{1,10}$.0$^{3,7}$] tetradecane in a form of a mixture comprising the diastereoisomers (1R,3S,5R,7R,8R,10S,13R) and (1R,3S, 5S,7R,8R,10S,13R) in a respective ratio of 59:41.

$^1$H-NMR (600 MHz, CDCl3): δ (ppm) 5.89-5.99 (overlapping dd, J 10.7, 17.5 Hz for major diastereomer (1R,3S, 5R,7R,8R,10S,13R), 0.67H), 5.32 (dd, J 1.8, 17.5 Hz for (1R,3S,5R,7R,8R,10S,13R)-diastereomer, major), 5.327 (dd, J 1.8, 17.5 Hz, for (1R,3S,5S,7R,8R,10S,13R)-diastereomer, minor, 0.43 H), 5.18 (dd, J 1.8, 10.8 Hz, for (1R,3S,5S,7R,8R,10S,13R)-diastereomer, minor, 0.43 H), 5.12 (dd, J 1.8, 10.8 Hz, for (1R,3S,5R,7R,8R,10S,13R)-diastereomer, major, 0.67H), 4.04-4.09 (2 overlapping t, J 7.8 Hz, 2H), 1.94-2.05 (m, 3H), 1.37-1.87 (m, 14H), 1.22-1.33 (m, 1H), 1.11-1.37 (two overlapping s, 3H), 1.02-1.05 (two overlapping s, 3H), 0.89-0.94 (m, 3H), 0.82 (d, J 7 Hz, 2H), 0.76 (d, J 7.2 Hz, 1H)

$^{13}$C (150 MHz, CDCl$_3$): δ (ppm) 8.46, 8.49, 15.3, 15.5, 25.4, 25.5, 26.9, 27.5, 28.67, 28.72, 30.98, 31.00, 34.4, 34.9, 35.7, 36.1, 38.45, 38.50, 38.7, 41.4, 41.8, 41.9, 42.4, 42.6, 52.6, 52.7, 57.48, 57.50, 58.28, 58.33, 76.8, 77.0, 77.2, 78.5, 78.9, 85.0, 85.2, 109.6, 109.7, 114.0, 114.4, 141.5, 141.6

Example 15

Synthesis of 5-ethyl-7,9,9,13-tetramethyl-5-[(1E)-1-propen-1-yl]-4,6-dioxatetracyclo[6.5.1.0$^{1,10}$.0$^{3,7}$] tetradecane in a Form of a Mixture Comprising the Diastereoisomers (1R,3S,5R,7R,8R,10S.13R) and (1R,3S,5S,7R,8R,10S.13R) in a Respective Ratio of 92:8 (Comparative Compound)

A 100 mL 3-neck round bottomed flask equipped with a magnetic stir bar and a reflux condenser was charged with 4 g of cedrenediol, 8.2 g of (E)-hex-4-en-3-one, 1.8 g of trimethylorthoformate, 70 mL of cyclohexane and cooled to 0° C. The slurry is then charged with 0.06 g of TMSOTf and stirred at 0° C. for 2.5 h then quenched by pouring it into saturated NaHCO$_3$ and diluted with ether. After phase separation, the aqueous phase was extracted twice with ether, washed with water, dried over Na$_2$SO$_4$ and concentrated on the rotovap to give 11 g of crude. The latter was purified by silica column chromatography using pentane/ether (95/5) to give 1.2 g of 96% pure 5-ethyl-7,9,9,13-tetramethyl-5-[(1E)-1-propen-1-yl]-4,6-dioxatetracyclo[6.5.1.0$^{1,10}$.0$^{3,7}$]tetradecane in a form of a mixture comprising the diastereoisomers (1R,3S,5R,7R,8R,10S,13R) and (1R,3S,5S,7R,8R,10S,13R) in a respective ratio of 92:8 which after bulb-to-bulb distillation led to 1.1 g of 97% pure 5-ethyl-7,9,9,13-tetramethyl-5-[(1E)-1-propen-1-yl]-4,6-dioxatetracyclo[6.5.1.0$^{1,10}$.0$^{3,7}$]tetradecane in a form of a mixture comprising the diastereoisomers (1R,3S,5R,7R,8R,10S,13R) and (1R,3S,5S,7R,8R,10S,13R) in a respective ratio of 92:8.

$^1$H-NMR (600 MHz, CDCl3): δ (ppm) 5.69-5.76 (m, 1H), 5.55 (dq, 1.6, 15.6 Hz, 1H), 4.06 (dd, 6.7, 9.2 Hz, 1H), 2.02 (d, 11.4 Hz, 1H), 1.92-1.99 (m, 2H), 1.68-1.87 (m, 7H), 1.38-1.64 (m, 9H), 1.29 (sextet, J 6.1 Hz, 1H), 1.14 (s, 3H), 1.03, (s, 3H), 0.91 (t, J 7.5 Hz, 3H), 0.82 (d, J 7.5 Hz, 3H)

$^{13}$C (150 MHz, CDCl$_3$): δ (ppm) 8.6, 15.5, 17.5, 25.4, 27.0, 28.7, 31.0, 34.7, 35.7, 38.5, 41.4, 41.8, 42.6, 52.6, 57.6, 58.3, 76.8, 77.0, 77.2, 78.4, 85.0, 109.7, 124.9, 134.5

Example 16

Synthesis of 5,7,9,9,13-pentamethyl-5-vinyl-4,6-dioxatetracyclo[6.5.1.0~$^{1,10}$~.0~$^{3,7}$~]tetradecane in a Form of a Mixture Comprising the Diastereoisomers (1R,3S,5R,7R,8R,10S,13R) and (1R,3S,5S,7R,8R,10S,13R) in a Respective Ratio of 88:12 (Comparative Compound)

A 100 mL 3-neck round bottomed flask equipped with a magnetic stir bar and a reflux condenser was charged with 4 g of cedrenediol, 5.9 g of 3-buten-2-one, 1.8 g of trimethylorthoformate, 70 mL of cyclohexane and cooled to 0° C. The slurry was then charged with 0.037 g of TMSOTf and stirred at 0° C. for 2 h then for 3 h at room temperature to partial conversion of the starting diol. The reaction is quenched by pouring it into saturated NaHCO$_3$ and diluted with ether. After phase separation, the aqueous phase was extracted twice with ether, washed with water, dried over Na$_2$SO$_4$ and concentrated on the rotovap to give 6.1 g of crude. The crude was charged with pentane in order to precipitate the unreacted cedrenediol. After filtering off the solid the mother liquour is re-concentrated to give 4.1 g of material which is purified by silica column chromatography using pentane/ether (97/3) to give 0.25 g of 95% pure 5,7,9,9,13-pentamethyl-5-vinyl-4,6-dioxatetracyclo[6.5.1.0~$^{1,10}$~.0~$^{3,7}$~]tetradecanein a form of a mixture comprising the diastereoisomers (1R,3S,5R,7R,8R,10S,13R) and (1R,3S,5S,7R,8R,10S,13R) in a respective ratio of 89:11.

$^1$H-NMR (600 MHz, CDCl3): δ (ppm) 6.04 (dd, J 10.8, 17.3 Hz, 1H), 5.34 (dd, J 1.9, 17.4, 1H), 5.04 (dd, J 1.4, 10.8, 1H), 4.08 (dd, J 7.2, 8.8 Hz, 1H), 1.93-2.06 (m, 3H), 1.72-1.88 (m, 3H), 1.49-1.66 (m, 9H), 1.38-1.48 (m, 5H), 1.30 (sextet, J 6.2 Hz, 1H), 1.15 (s, 3H), 1.04 (s, 3H), 0.83 (d, J 7 Hz, 3H)

$^{13}$C (150 MHz, CDCl$_3$): δ (ppm) 15.4, 25.4, 26.7, 28.68, 26.72, 28.84, 31.0, 35.8, 38.49, 38.52, 41.3, 41.8, 42.6, 52.6, 57.5, 58.3, 76.8, 77.0, 77.2, 78.6, 85.5, 107.5, 112.8, 143.5

Example 17

Synthesis of 5,7,9,9,13-pentamethyl-5-(2-methyl-1-propen-1-yl)-4,6-dioxatetracyclo [6.5.1.0~$^{1,10}$~.0~$^{3,7}$~]tetradecane in a Form of a Mixture Comprising the Diastereoisomers (1R,3S,5R,7R,8R,10S,13R) and (1R,3S,5S,7R,8R,10S,13R) in a Respective Ratio of 67:33 (Comparative Compound)

A 100 mL 3-neck round bottomed flask equipped with a magnetic stir bar and a reflux condenser was charged with 5 g of cedrenediol, 10.3 g of 4-methyl-3-penten-2-one, 2.2 g of trimethylorthoformate, 120 mL of cyclohexane and cooled to 0° C. The slurry was then charged with 0.035 g of TMSOTf and stirred at 0° C. for 3 h to partial conversion of the starting diol. The reaction is quenched by pouring it into saturated NaHCO$_3$ and diluted with ether. After phase separation, the aqueous phase was extracted twice with ether, washed with water, dried over Na$_2$SO$_4$ and concentrated on the rotovap to give 17 g of crude. The crude was flushed through a 7 cm diameter silica column using first pure pentane, followed by a pentane/ether gradient 97/3 then 95/5 to give 2.71 g of 49% pure 5,7,9,9,13-pentamethyl-5-(2-methyl-1-propen-1-yl)-4,6-dioxatetracyclo [6.5.1.0~$^{1,10}$~.0~$^{3,7}$~]tetradecane in a form of a mixture comprising diastereoisomers (1R,3S,5R,7R,8R,10S,13R) and (1R,3S,5S,7R,8R,10S,13R) in a respective ratio of 88:12 which crystallized upon standing. The solid was then carefully distilled on the kuegel-rohr to remove lighter components which led to 2.04 g of 96% pure 5,7,9,9,13-pentamethyl-5-(2-methyl-1-propen-1-yl)-4,6-dioxatetracyclo [6.5.1.0~$^{1,10}$~.0~$^{3,7}$~]tetradecane in a form of a mixture comprising the diastereoisomers (1R,3S,5R,7R,8R,10S,13R) and (1R,3S,5S,7R,8R,10S,13R) in a respective ratio of 94/6. The distilled material was further recrystallized in hexane. After filtering and rinsing the crystals in cold hexane 1.12 g of 97% pure (1R,3S,5R,7R,8R,10S,13R)-5,7,9,9,13-pentamethyl-5-(2-methyl-1-propen-1-yl)-4,6-dioxatetracyclo [6.5.1.0~$^{1,10}$~.0~$^{3,7}$~]tetradecane was obtained. The mother liquour was concentrated on the rotovap and the solid residue was recrystallized to give a 2$^{nd}$ crop of 0.21 g of (1R,3S,5R,7R,8R,10S,13R)-5,7,9,9,13-pentamethyl-5-(2-methyl-1-propen-1-yl)-4,6-dioxatetracyclo [6.5.1.0~$^{1,10}$~.0~$^{3,7}$~]tetradecane at 97% purity. The resulting mother liquour was concentrated then bulb-to-bulb distilled to give 0.32 g of 97% pure, 7,9,9,13-pentamethyl-5-(2-methyl-1-propen-1-yl)-4,6-dioxatetracyclo [6.5.1.0~$^{1,10}$~.0~$^{3,7}$~]tetradecane in a form of a mixture comprising the diastereoisomers (1R,3S,5R,7R,8R,10S,13R) and (1R,3S,5S,7R,8R,10S,13R) in a respective ratio of 67/33.

$^1$H-NMR (600 MHz, CDCl3): δ (ppm) 5.45 (broad singlet, 1H), 4.01 (t, J 7.5 Hz, 1H), 2.04 (d, J 11.9 Hz, 1H), 1.91-1.96 (m, 2H), 1.84 (sextet, J 6.1 Hz 1H), 1.79 (s, 3H), 1.75 (sextet, J 7.3 Hz 1H), 1.48-1.68 (m, 10H), 1.38-1.47 (m, 4H), 1.24-1.32 (m, 1H), 1.14 (s, 3H), 1.03 (s, 3H), 0.82 (d, J 7.3 Hz, 3H)

$^{13}$C (150 MHz, CDCl$_3$): δ (ppm) 15.5, 18.8, 25.4, 25.7, 26.3, 28.7, 29.3, 30.9, 35.9, 38.6, 41.3, 41.8, 42.6, 52.7, 57.4, 58.1, 76.8, 77.0, 77.2, 78.0, 84.9, 108.1, 131.8, 132.1

Example 18

Synthesis of 5-isopropenyl-5,7,9,9,13-pentamethyl-4,6-dioxatetracyclo[6.5.1.0~$^{1,10}$~.0~$^{3,7}$~]tetradecane in a Form of a Mixture Comprising the Diastereoisomers (1R,3S,5R,7R,8R,10S,13R) and (1R,3S,5S,7R,8R,10S,13R) in a Respective Ratio of 79:21 (Comparative Compound)

A 250 mL 3-neck round bottomed flask equipped with a magnetic stir bar and a reflux condenser was charged with 5 g of cedrenediol, 8.8 g of 3-methylbut-3-en-2-one, 2.2 g of trimethylorthoformate, 120 mL of cyclohexane and cooled to 0° C. The slurry was then charged with 0.035 g of TMSOTf and stirred at 0° C. for 6 h then quenched by pouring it into saturated NaHCO$_3$ and diluted with ether. After phase separation, the aqueous phase was extracted twice with ether, washed with water, dried over Na$_2$SO$_4$ and concentrated on the rotovap to give 15 g of crude. The latter was purified by silica column chromatography using a gradient of pentane/ether (97/3 then 95/5) to give 1.55 g of 95% pure 5-isopropenyl-5,7,9,9,13-pentamethyl-4,6-dioxatetracyclo[6.5.1.0~$^{1,10}$~.0~$^{3,7}$~]tetradecane. Following bulb-to-bulb distillation, 1.37 g of 91% pure 5-isopropenyl-5,7,9,9,13-pentamethyl-4,6-dioxatetracyclo[6.5.1.0~$^{1,10}$~. 0~$^{3,7}$~]tetradecane in a form of a mixture comprising the diastereoisomers (1R,3S,5R,7R,8R,10S,13R) and (1R,3S,5S,7R,8R,10S,13R) in a respective ratio of 79/21 was obtained, which crystallized upon standing.

$^1$H-NMR (600 MHz, CDCl3): δ (ppm) 5.15 (d, J 1.6 Hz, 1H), 4.75 (d, J 1.6 Hz, 1H), 4.06 (t, J 8.4 Hz, 1H), 1.93-2.06 (m, 3H), 1.22-1.89 (m, 20H), 1.14 (s, 3H), 1.03 (s, 3H), 0.83 (d, J 7.6 Hz, 3H)

$^{13}$C (150 MHz, CDCl$_3$): δ (ppm) 15.4, 19.1, 25.4, 25.5, 25.8, 28.4, 28.7, 31.0, 35.8, 38.6, 41.5, 41.78, 41.81, 42.6, 52.6, 57.5, 58.2, 76.8, 77.0, 77.2, 78.5, 85.3, 109.1, 109.6, 150.2

Example 19

Synthesis of 5-[(2E)-2-buten-2-yl]-5,7,9,9,13-pentamethyl-4,6-dioxatetracyclo[6.5.1.0~$^{1,10}$~.0~$^{3,7}$~] tetradecane in a Form of a Mixture Comprising the Diastereoisomers (1R,3S,5R,7R,8R,10S,13R) and (1R,3S,5S,7R,8R,10S,13R) in a Respective Ratio of 78:22 (Comparative Compound)

A 100 mL 3-neck round bottomed flask equipped with a magnetic stir bar and a reflux condenser was charged with 5 g of cedrenediol, 10.3 g of (E)-3-methylpent-3-en-2-one, 2.2 g of trimethylorthoformate, 75 mL of cyclohexane and cooled to 0° C. The slurry was then charged with 0.06 g of TMSOTf and stirred at 0° C. for 6 h then quenched by pouring it into saturated NaHCO$_3$ and diluted with ether. After phase separation, the aqueous phase was extracted twice with ether, washed with water, dried over Na$_2$SO$_4$ and concentrated on the rotovap to give 12.5 g of crude. The latter was purified by silica column chromatography using pentane/ether (95/5) to give 1.2 g of 96% pure 5-[(2E)-2-buten-2-yl]-5,7,9,9,13-pentamethyl-4,6-dioxatetracyclo [6.5.1.0~$^{1,10}$~.0~$^{3,7}$~]tetradecane. Following bulb-to-bulb distillation, 1.19 g of 96% pure 5-[(2E)-2-buten-2-yl]-5,7,9,9,13-pentamethyl-4,6-dioxatetracyclo[6.5.1.0~$^{1,10}$~. 0~$^{3,7}$~]tetradecane in a form of a mixture comprising the diastereoisomers (1R,3S,5R,7R,8R,10S,13R) and (1R,3S,5S,7R,8R,10S,13R) in a respective ratio of 78:22 was obtained, which crystallized upon standing.

$^1$H-NMR (600 MHz, CDCl3): δ (ppm) 5.67-5.76 (m, 1H), 4.01, 4.06 (m, 1H), 1.93-2.06 (m, 3H), 1.20-1.88 (m, 22H), 1.13 (s, 3H), 1.03 (s, 3H), 0.82 (d, J 7.5, 3H)

$^{13}$C (150 MHz, CDCl$_3$): δ (ppm) 12.6, 13.0, 15.4, 25.4, 25.8, 28.6, 28.7, 31.0, 35.8, 38.6, 41.5, 41.8, 42.6, 52.6, 57.62, 57.64, 58.3, 76.8, 77.0, 77.2, 78.5, 85.0, 109.6, 117.4, 140.5

Example 20

Synthesis of 1R,3S,5R,7R,8R,10S,13R)-5-ethynyl-5,7,9,9,13-pentamethyl-4,6-dioxatetracyclo[6.5.1. 0$^{1,10}$.0$^{3,7}$]tetradecane (Comparative Compound)

25 mL schlenk tube equipped with a mag stir bar and dean-stark trap was charged with 0.13 g of Al$_2$(SO$_4$)$_3$ octadecahydrate, 0.9 g of cedrenediol, 15 mL of cyclohexane and 1.3 g of 3,3-dimethoxy-1-butyne. The mixture was placed under N$_2$ atmosphere and heated to reflux at an oil bath temperature of 88° C. for 46 h then quenched by pouring it into saturated NaHCO$_3$. After phase separation, the aqueous phase was extracted 2× with ether, combined, dried over Na$_2$SO$_4$, filtered and concentrated to give 1.18 g of waxy oil. The latter was chromatographed on silica using 15:1 pentane/ether to give 0.109 g of (1R,3S,5R,7R,8R,10 S,13R)-5-ethynyl-5,7,9,9,13-pentamethyl-4,6-dioxatetracyclo[6.5.1.0$^{1,10}$.0$^{3,7}$]tetradecane.

$^1$H-NMR (600 MHz, C$_6$D$_6$): δ (ppm) 4.0 (dd, J 7.1, 9.1 Hz, 1H), 2.62 (dd, J 7.1, 9.1 Hz, 1H), 2.49 (d, J 12 Hz, 1H), 2.16 (s, 1H), 1.97 (d, J 4.4 Hz, 1H), 1.85 (s, 3H), 1.68-1.79 (m, 3H), 1.48-1.52 (m, 1H), 1.36-1.41 (m, 4H), 1.26-1.32 (m, 2H), 1.16-1.22 (m, 1H), 0.9-0.93 (s, 3H), 0.85-0.88 (m, 6H)

$^{13}$C (150 MHz, C$_6$D$_6$): δ (ppm) 128.32, 128.19, 128.10, 128.03, 127.95, 127.87, 100.53, 86.40, 86.07, 80.42, 71.99, 58.67, 57.78, 52.37, 42.48, 42.04, 39.22, 38.29, 36.62, 31.52, 30.78, 28.69, 27.91, 25.83, 15.63

Example 21

Preparation of a Perfuming Composition

A perfuming composition for a men fine fragrance, dosed at 15% in the final product, was prepared by admixing the following ingredients:

| Ingredient | Parts by weight |
|---|---|
| Ambrox ®[1] super | 800 |
| Amyl salicylate | 80 |
| 10%* ethyl 2-methylpentanoate | 80 |
| Citronellol | 100 |
| Clearwood ®[2] | 100 |
| 4-cyclohexyl-2-methyl-2-butanol | 400 |
| Coumarin | 100 |
| Damascone alpha | 10 |
| Dihydromyrcenol | 800 |
| Floralozone[3] | 10 |
| Habanolide ®[4] | 800 |
| Hedione ®[5] HC | 1000 |
| (+−)-3-(1,3-benzodioxol-5-yl)-2-methylpropanal | 100 |
| Helvetolide ®[6] | 200 |
| Hivernal ®[7] | 20 |
| Iso E ® super[8] | 3000 |
| Lavender oil | 80 |
| Lemon oil | 400 |
| 6,6-dimethoxy-2,5,5-trimethyl-2-hexene | 200 |
| Methyl 2,4-dihydroxy-3,6-dimethylbenzoate | 100 |
| 10%* neobutenone ®[9] alpha | 80 |
| Nirvanol ®[10] | 100 |
| Patchouli oil | 300 |
| Pink pepper oil | 80 |
| (Z)-3-hexen-1-ol | 10 |
| (3Z)-3-hexen-1-yl salicylate | 80 |
| Rhubofix ®[11] | 10 |
| Scentenal ®[12] | 10 |
| Sclareolate ®[13] | 200 |
| (+−)-1-phenylethyl acetate | 40 |
| (+−)-2-ethyl-4,4-dimethylcyclohexanone | 10 |
| Mixture of 1-[2,6,10-trimethyl-1,5,9-cyclododecatrien-1-yl]ethanone, 1-[-4,8-dimethyl- | 200 |

-continued

| Ingredient | Parts by weight |
| --- | --- |
| 12-methylene-4,8-cyclododecadien-1-yl]ethanone and 1-[-2,6,10-trimethyl-2,5,9-cyclododecatrien-1-yl]ethanone | |
| 2-tert-butyl-1-cyclohexyl acetate | 200 |
| Vetyver oil | 100 |
| Dipropylene glycol | 200 |
| | 10000 |

*in dipropyleneglycol
[1])(−)-(8R)-8,12-epoxy-13,14,15,16-tetranorlabdane; origin: Firmenich SA, Geneva, Switzerland
[2])origin: Firmenich SA, Geneva, Switzerland
[3])3-(4/2-Ethylphenyl)-2,2-dimethylpropanal; origin: International Flavors & Fragrances, USA
[4])Pentadecenolide; origin: Firmenich SA, Geneva, Switzerland
[5])dihydrojasmonate with high amount of cis isomer; origin: Firmenich SA, Geneva, Switzerland
[6])(1S,1'R)-2-[1-(3',3'-dimethyl-1'-cyclohexyl)ethoxy]-2-methylpropyl propanoate; origin: Firmenich SA, Geneva, Switzerland
[7])3-(3,3/1,1-dimethyl-5-indanyl)propanal; origin: Firmenich SA, Geneva, Switzerland
[8])1-(octahydro-2,3,8,8-tetramethyl-2-naphtalenyl)-1-ethanone; origin: International Flavors & Fragrances, USA
[9])1-(5,5-dimethyl-1-cyclohexen-1-yl)-4-penten-1-one; origin: Firmenich SA, Geneva, Switzerland
[10])3,3-dimethyl-5-(2,2,3-trimethyl-3-cyclopenten-1-yl)-4-penten-2-ol; origin: Firmenich SA, Geneva, Switzerland
[11])(+−)-3,4'-dimethylspiro[oxirane-2,9'-tricyclo[6.2.1.0$^{2,7}$]undec[4]ene; origin: Firmenich SA, Geneva, Switzerland
[12])8(9)-methoxy-tricyclo[5.2.1.0.(2,6)]decane-3(4)-carbaldehyde; origin: Firmenich SA, Geneva, Switzerland
[13])Propyl (S)-2-(1,1-dimethylpropoxy)propanoate; origin: Firmenich SA, Geneva, Switzerland The addition of 200 parts by weight of a solution containing 10% of 5,7,9,9,13-pentamethyl-5-[(1E)-1-propen-1-yl]-4,6-dioxatetracyclo[6.5.1.0$^{1,10}$.0$^{3,7}$]tetradecane in a form of a mixture comprising the diastereoisomers (1R,3S,5R,7R,8R,10S,13R) and (1R,3S,5S,7R,8R,10S,13R) in a respective ratio of 85:15 in dipropylene glycol to replace 200 parts by weight of dipropylene glycol in the above-described composition imparted to the latter a reinforced woody-dry and ambery connotation which was stronger, clearer and more linear and perceived even after 24 h on top note. The performance is outstanding on top and even after 24 h.

Similar effect was obtained when a same amount of a solution containing 10% of (−)-(1R,3S,5R,7R,8R,10S,13R)-5,7,9,9,13-pentamethyl-5-(1-propyn-1-yl)-4,6-dioxatetracyclo[6.5.1.0$^{1,10}$.0$^{3,7}$]tetradecane in dipropylene glycol was used to replace 200 parts by weight of dipropylene glycol.

When instead of the invention's compound, the same amount of a solution containing 10% of Ambrocenide® ((−)-(1R,3S,7R,8R,10S,13R)-5,5,7,9,9,9,13-hexamethyl-4,6-dioxatetracyclo[6.5.1.0$^{1,10}$.0$^{3,7}$]tetradecane; origin Symrise, Germany) in dipropylene glycol was used to replace 200 parts by weight of dipropylene glycol, the composition acquired a woody-dry connotation but also comprising animalic note, in particular on the top, which was decreased a lot after 24 h hours.

When instead of the invention's compound, the same amount of a solution containing 10% of a mixture comprising (1R,3S,5R,7R,8R,10S,13R)-5,7,9,9,13-pentamethyl-5-propyl-4,6-dioxatetracyclo[6.5.1.0$^{1,10}$.0$^{3,7}$]tetradecane and (1R,3S,5S,7R,8R,10S,13R)-5,7,9,9,13-pentamethyl-5-propyl-4,6-dioxatetracyclo[6.5.1.0$^{1,10}$.0$^{3,7}$]tetradecane as reported in example I of US 20120077722 in dipropylene glycol was used to replace 200 parts by weight of dipropylene glycol, the composition acquired a warm-ambery connotation with volume. The effect was more subtle than with Ambrocenide® but was more constant across the time and was still perceived after 24 h.

The impact on the overall composition was clearly superior with the invention compound than with both prior art ingredients. Even when 5 times less of the invention compound was added to the above-composition compared to Ambrocenide® or to compound exemplified in example 1 of US 20120077722, the invention compound is still more powerful and more substantive in bottom and top notes.

The invention's compounds from example 1 and example 4 possess a bottom and top not clearly more powerful than both prior ingredients.

Example 22

Preparation of a Perfuming Composition

A perfuming composition for liquid detergent, dosed at 1.5% in the final product, was prepared by admixing the following ingredients:

| Ingredient | Parts by weight |
| --- | --- |
| (+−)-2-methylundecanal | 300 |
| Benzyl acetate | 350 |
| Cetalox ®[1]) | 10 |
| Citronellol | 800 |
| 4-cyclohexyl-2-methyl-2-butanol | 1000 |
| (+−)-2,6-dimethyl-7-octen-2-ol | 2000 |
| Geraniol | 200 |
| Hedione ®[2]) | 100 |
| Helvetolide ®[3]) | 200 |
| Hexyl salicylate | 1000 |
| Hivemal ®[4]) | 100 |
| Iso E ®[5]) Super | 800 |
| Neobutenone ®[6])alpha | 10 |
| Phenylhexanol | 400 |
| Tetrahydro-4-methyl-2-(2-methyl-1-propenyl)-2h-pyran | 20 |
| Salicynile ®[7]) | 200 |
| (+−)-2-ethyl-4,4-dimethylcyclohexanone | 10 |
| 2-tert-butyl-1-cyclohexyl acetate | 1400 |
| Verdyl propionate | 1000 |
| Dipropylene glycol | 100 |
| | 10000 |

[1])dodecahydro-3a,6,6,9a-tetramethyl-naphtho[2,1-b]furan; origin: Firmenich SA, Geneva, Switzerland
[2])dihydrojasmonate with high amount of cis isomer; origin: Firmenich SA, Geneva, Switzerland
[3])(1S,1'R)-2-[1-(3',3'-dimethyl-1'-cyclohexyl)ethoxy]-2-methylpropyl propanoate; origin: Firmenich SA, Geneva, Switzerland
[4])3-(3,3/1,1-dimethyl-5-indanyl)propanal; origin: Firmenich SA, Geneva, Switzerland
[5])1-(octahydro-2,3,8,8-tetramethyl-2-naphtalenyl)-1-ethanone; origin: International Flavors & Fragrances, USA
[6])1-(5,5-dimethyl-1-cyclohexen-1-yl)-4-penten-1-one; origin: Firmenich SA, Geneva, Switzerland
[7])(2Z)-2-phenyl-2-hexenenitrile; origin: Firmenich SA, Geneva, Switzerland The addition of 100 parts by weight of a solution containing 10% of 5,7,9,9,13-pentamethyl-5-[(1E)-1-propen-1-yl]-4,6-dioxatetracyclo[6.5.1.0$^{1,10}$.0$^{3,7}$]tetradecane in a form of a mixture comprising the diastereoisomers (1R,3S,5R,7R,8R,10S,13R) and (1R,3S,5S,7R,8R,10S,13R) in a respective ratio of 85:15 in dipropylene glycol to replace 100 parts by weight of dipropylene glycol in the above-described composition imparted to the latter a reinforced woody-dry and ambery connotation which was stronger. Said note bringing by the invention compound is highly perceived on neat, on damp and dry cloths. The invention's compound is so powerful that it was perceived to be overdosed.

Similar effect was obtained when a same amount of a solution containing 10% of (−)-(1R,3S,5R,7R,8R,10S,13R)-5,7,9,9,13-pentamethyl-5-(1-propyn-1-yl)-4,6-dioxatetracyclo[6.5.1.0$^{1,10}$.0$^{3,7}$]tetradecane in dipropylene glycol was used to replace 200 parts by weight of dipropylene glycol.

When instead of the invention's compound, the same amount of a solution containing 10% of Ambrocenide® ((−)-(1R,3S,7R,8R,10S,13R)-5,5,7,9,9,9,13-hexamethyl-4,6-dioxatetracyclo[6.5.1.0(1,10).0(3,7)]tetradecane; origin Symrise, Germany) in dipropylene glycol was used to replace 100 parts by weight of dipropylene glycol, the composition acquired a woody-dry connotation but also comprising animalic note particularly detectable on neat and on damp cloths but with much less impact on dry cloths.

When instead of the invention's compound, the same amount of a solution containing 10% of a mixture comprising (1R,3S,5R,7R,8R,10S,13R)-5,7,9,9,13-pentamethyl-5-propyl-4,6-dioxatetracyclo[6.5.1.0$^{1,10}$.0$^{3,7}$]tetradecane and (1R,3S,5S,7R,8R,1S,13R)-5,7,9,9,13-pentamethyl-5-propyl-4,6-dioxatetracyclo[6.5.1.0$^{1,10}$.0$^{3,7}$]tetradecane as reported in example I of US 20120077722 in dipropylene glycol was used to replace 100 parts by weight of dipropylene glycol, the composition acquired a warm-ambery connotation with volume which is observed on neat, on damp cloths and with a lower extent on dry cloths.

Example 23

Preparation of a Eau De Toilette Comprising the Invention's Compound

The eau de toilette was prepared by adding 15% by weight, relative to the total weight of the eau de toilette, of the invention's composition of example 21 into ethanol under gentle shaking.

Example 24

Preparation of a Liquid Detergent Comprising the Invention's Compound

TABLE 2

Composition of the liquid detergent formulation

| Ingredients | Concentration [wt %] |
| --- | --- |
| Sodium C14-17 Alkyl Sec Sulfonate[1] | 7 |
| Fatty acids, C12-18 and C18-unsaturated[2] | 7.5 |
| C12/14 fatty alcohol polyglycol ether with 7 mol EO[3] | 17 |
| Triethanolamine | 7.5 |
| Propylene Glycol | 11 |
| Citric acid | 6.5 |
| Potassium Hydroxyde | 9.5 |
| Properase L[4] | 0.2 |
| Puradax EG L[4] | 0.2 |
| Purastar ST L[4] | 0.2 |
| Acrylates/Steareth-20 Methacrylate structuring Crosspolymer[5] | 6 |
| Deionized Water | 27.4 |

[1]Hostapur SAS 60; Origin: Clariant
[2]Edenor K 12-18; Origin: Cognis
[3]Genapol LA 070; Origin: Clariant
[4]Origin: Genencor International
[5]Aculyn 88; Origin: Dow Chemical The liquid detergent was prepared by adding 0.5 to 1.5% by weight, relative to the total weight of the liquid detergent, of the invention's composition of example 22 into the unperfumed liquid detergent formulation of Table 2 under gentle shaking.

Example 25

Measurement of the Subtantivity of the Invention's Compound

Fabrics (2.0 kg of cotton or polyester terry towels) were washed at 40° C. in a standard European horizontal axis machine (Miele Novotronic W 900-79 CH). There were dispensed 75 g of freshly prepared liquid detergent of Table 2 comprising 0.5% of a dipropylene glycol solution containing 1% of the invention's compound of example 1 or 1% of the prior art compounds at the start of the wash through the detergent drawer. The odor intensity of the fabrics was evaluated by a panel of 4 trained panelists after the wash and also after fabrics were line-dried overnight. The odor intensity of the detergent was also evaluated by a panel of 4 trained panelists. The panelists were asked to rate the odor intensity of the towels and of the detergent on a scale from 1 to 10, 1 corresponding to odorless and 10 corresponding to a very strong odor.

TABLE 3

| Compound tested | Evaluation by panelist | | | | |
| --- | --- | --- | --- | --- | --- |
| | Neat | wet fabric | | dry fabric | |
| | | Coton | Polyester | Coton | Polyester |
| Ambrocenide ® | 6.25 | 5.7 | 5.7 | 3.3 | 3.7 |
| compound exemplified in example 1 of US 20120077722 | 6.25 | 5.7 | 5.7 | 3.3 | 4.0 |
| compound from Example 1 | 8.5 | 8.7 | 8.7 | 5.7 | 6.3 |

The below-result clearly demonstrates that the invention's compound at the same concentration overperforms compared to the prior art compounds in all stage; i.e. neat, wet fabric or dry fabric no matter the type of fabrics.

Example 26

Preparation of a Fabric Softener Comprising the Invention's Compound

TABLE 4

Composition of the softener formulation

| Ingredient | Concentration [wt %] |
| --- | --- |
| Methyl bis[ethyl (tallowate)]-2-hydroxyethyl ammonium methyl sulfate[1] | 12.20 |
| 1,2-benzisothiazolin-3-one[2] | 0.04 |
| CaCl$_2$ (10% aqueous solution) | 0.40 |
| Water | 87.36 |

[1]Stepantex VL90 A Diester Quat; Origin: Stepan
[2]Proxel GXL; Origin: Arch

The softener was prepared by weighting Methyl bis[ethyl (tallowate)]-2-hydroxyethyl ammonium methyl sulfate which was heated at 65° C. Then Water and 1,2-benzisothiazolin-3-one were placed in the reactor and were heated at 65° C. under stirring. To the above mixture was added Methyl bis[ethyl (tallowate)]-2-hydroxyethyl ammonium methyl sulfate. The mixture was stirred 15 minutes and CaCl$_2$ was added. Then 0.5 to 2% by weight, relative to the total weight of the softener, of the invention's composition of example 23 was added. The mixture was stirred 15 minutes and was cooled down to room temperature under stirring (viscosity measure: result 35+/−5 mPas. (shear rate 106 sec-1)).

Example 27

Preparation of a Transparent Isotropic Shampoo Comprising the Invention's Composition

TABLE 5

Composition of the transparent isotropic shampoo formulation

| Phases | Ingredients | Concentration [wt %] |
|---|---|---|
| A | Water deionized | 44.4 |
|  | Polyquaternium-10 [1] | 0.3 |
|  | Glycerin 85% [2] | 1 |
|  | DMDM Hydantoin [3] | 0.2 |
| B | Sodium Laureth Sulfate [4] | 28 |
|  | Cocamidopropyl Betaine [5] | 3.2 |
|  | Disodium Cocoamphodiacetate [6] | 4 |
|  | Ethoxy (20) Stearyl Alcohol [6] | 1 |
| C | Sodium Laureth Sulfate [4] | 3 |
|  | Glyceryl Laureate [7] | 0.2 |
| D | Water deionized | 1 |
|  | Sodium Methylparaben [8] | 0.1 |
| E | Sodium Chloride 10% aqueous sol. | 15 |
|  | Citric acid 10% aqueous sol. till pH 5.5-6 | q.s. |

[1] Ucare Polymer JR-400, Origin: Noveon
[2] Origin: Schweizerhall
[3] Glydant, Origin: Lonza
[4] Texapon NSO IS, Origin: Cognis
[5] Tego Betain F 50, Origin: Evonik
[6] Amphotensid GB 2009, Origin: Zschimmer & Schwarz
[7] Monomuls 90 L-12, Origin: Gruenau
[8] Nipagin Monosodium, Origin: NIPA The shampoo was prepared by dispersed in water Polyquarternium-10. The remaining ingredients of phase A were mixed separately by addition of one after the other while mixing well after each adjunction. This pre-mix was added to the Polyquarternium-10 dispersion and mixed for another 5 min. Then, the premixed phase B and the premixed Phase C were added (Monomuls 90 L-12 was heated to melt in Texapon NSO IS) while agitating. Phase D and Phase E were added while agitating. PH was adjusted with citric acid solution till pH: 5.5-6.0 leading to an unperfumed shampoo formulae.

The perfumed shampoo was prepared by adding 0.4 to 0.8% by weight, relative to the total weight of the shampoo, of the invention's composition of example 23 into the unperfumed shampoo formulation of Table 5 under gentle shaking.

Example 28

Preparation of a Structured Shower Gel Comprising the Invention's Composition

TABLE 6

Composition of the shower gel formulation

| Ingredients | Amount (% wt) |
|---|---|
| WATER deionised | 49.350 |
| Tetrasodium EDTA [1] | 0.050 |
| Acrylates Copolymer [2] | 6.000 |
| Sodium C12-C15 Pareth Sulfate [3] | 35.000 |
| Sodium Hydroxide 20% aqueous solution | 1.000 |
| Cocamidopropyl Betaine [4] | 8.000 |
| Methylchloroisothiazolinone and Methylisothiazolinone [5] | 0.100 |
| Citric Acid (40%) | 0.500 |

[1] EDETA B POWDER; trademark and origin: BASF
[2] CARBOPOL AQUA SF-1 POLYMER; trademark and origin: NOVEON
[3] ZETESOL AO 328 U; trademark and origin: ZSCHIMMER & SCHWARZ
[4] TEGO-BETAIN F 50; trademark and origin: GOLDSCHMIDT
[5] KATHON CG; trademark and origin: ROHM & HASS The shower gel was prepared by adding 0.5 to 1.5% by weight, relative to the total weight of the shower gel, of the invention's composition of example 23 into the unperfumed shower gel formulation of Table 6 under gentle shaking.

Example 29

Preparation of a Transparent Shower Gel Comprising the Invention's Composition

TABLE 7

Composition of the transparent shower gel formulation

| Ingredients | Concentration (% wt) |
|---|---|
| WATER deionized | 52.40 |
| Tetrasodium EDTA [1] | 0.10 |
| Sodium Benzoate | 0.50 |
| Propylene Glycol | 2.00 |
| Sodium C12-C15 Pareth Sulfate [2] | 35.00 |
| Cocamidopropyl Betaine [3] | 8.00 |
| Polyquaternium-7 [4] | 0.20 |
| Citric Acid (40%) | 1.00 |
| Sodium Chloride | 0.80 |

[1] EDETA B POWDER; trademark and origin: BASF
[2] ZETESOL AO 328 U; trademark and origin: ZSCHIMMER & SCHWARZ
[3] TEGO-BETAIN F 50; trademark and origin: GOLDSCHMIDT
[4] MERQUAT 550; trademark and origin: LUBRIZOL The transparent shower gel was prepared by adding 0.5 to 1.5% by weight, relative to the total weight of the shower gel, of the invention's composition of example 23 into the unperfumed shower gel formulation of Table 7 under gentle shaking.

Example 30

Preparation of a Milky Shower Gel Comprising the Invention's Composition

TABLE 8

Composition of the milky shower gel formulation

| Ingredients | Concentration (% wt) |
|---|---|
| WATER deionized | 50.950 |
| Tetrasodium EDTA [1] | 0.050 |
| Sodium Benzoate | 0.500 |
| Glycerin 86% | 3.500 |
| Sodium Laureth Sulfate [2] | 27.000 |
| Polyquaternium-7 [3] | 1.000 |
| Coco-Betaine [4] | 6.000 |
| PEG-120 Methyl Glucose trioleate [5] | 1.000 |
| Citric Acid (40%) | 1.000 |
| Glycol Distearate & Laureth-4 & Cocamidopropyl Betaine [6] | 3.000 |

TABLE 8-continued

Composition of the milky shower gel formulation

| Ingredients | Concentration (% wt) |
| --- | --- |
| Sodium Chloride 20% | 5.000 |
| PEG-40 Hydrogenated Castor Oil[7] | 1.000 |

[1] EDETA B POWDER; trademark and origin: BASF
[2] Texapon NSO IS; trademark and origin: COGNIS
[3] MERQUAT 550; trademark and origin: LUBRIZOL
[4] DEHYTON AB-30; trademark and origin: COGNIS
[5] GLUCAMATE LT; trademark and origin: LUBRIZOL
[6] EUPERLAN PK 3000 AM; trademark and origin: COGNIS
[7] CREMOPHOR RH 40; trademark and origin: BASF The transparent shower gel was prepared by adding 0.5 to 1.5% by weight, relative to the total weight of the shower gel, of the invention's composition of example 23 into the unperfumed shower gel formulation of Table 8 under gentle shaking.

Example 31

Preparation of a Pearly Shampoo Comprising the Invention's Composition

TABLE 9

Composition of the pearly isotropic shampoo formulation

| Phases | Ingredients | Concentration (% wt) |
| --- | --- | --- |
| A | Water deionized | 45.97 |
| | Tetrasodium EDTA [1] | 0.05 |
| | Guar Hydroxypropyltrimonium Chloride [2] | 0.05 |
| | Polyquaternium-10 [3] | 0.075 |
| B | NaOH 10% aqueous sol. | 0.3 |
| C | Ammonium Lauryl Sulfate [4] | 34 |
| | Ammonium Laureth Sulfate [5] | 9.25 |
| | Cocamidopropyl Betaine [6] | 2 |
| | Dimethicone (&) C12-13 Pareth-4 (&) C12-13 Pareth-23 (&) Salicylic Acid [7] | 2.5 |
| D | Cetyl Alcohol [8] | 1.2 |
| | Cocamide MEA [9] | 1.5 |
| | Glycol Distearate [10] | 2 |
| E | Methylchloroisothiazolinone & Methylisothiazolinone [11] | 0.1 |
| | D-Panthenol 75% [12] | 0.1 |
| | Water deionized | 0.3 |
| F | Sodium Chloride 25% aqueous sol. | 0.6 |

[1] EDETA B Powder, Origin: BASF
[2] Jaguar C14 S, Origin: Rhodia
[3] Ucare Polymer JR-400, Origin: Noveon
[4] Sulfetal LA B-E, Origin: Zschimmer & Schwarz
[5] Zetesol LA, Origin: Zschimmer & Schwarz
[6] Tego Betain F 50, Origin: Evonik
[7] Xiameter MEM-1691, Origin: Dow Corning
[8] Lanette 16, Origin: BASF
[9] Comperlan 100, Origin: Cognis
[10] Cutina AGS, Origin: Cognis
[11] Kathon CG, Origin: Rohm & Haas
[12] D-Panthenol, Origin: Roche The shampoo was prepared by dispersed in water and Tetrasodium EDTA, Guar Hydroxypropyltrimonium Chloride and Polyquarternium-10. NaOH 10% solution (Phase B) was added once Phase A was homogeneous. Then, the premixed Phase C was added, and mixture was heated to 75° C. Phase D ingredients were added and mixed till homogeneous. The mixture was cooled down. At 45° C., Phase E ingredients were added while mixing. Final viscosity was adjusted with 25% NaCl solution and pH of 5.5-6 was adjusted with 10% NaOH solution.

The perfumed pearly shampoo was prepared by adding 0.4 to 0.8% by weight, relative to the total weight of the shampoo, of the invention's composition of example 23 into the unperfumed shampoo formulation of Table 9 under gentle shaking.

Example 32

Preparation of a Structured Shower Gel Comprising the Invention's Composition

TABLE 10

Composition of the milky shower gel formulation

| Ingredients | Amount (% wt) |
| --- | --- |
| WATER deionised | 49.350 |
| Tetrasodium EDTA [1] | 0.050 |
| Acrylates Copolymer[2] | 6.000 |
| Sodium C12-C15 Pareth Sulfate [3] | 35.000 |
| Sodium Hydroxide 20% aqueous solution | 1.000 |
| Cocamidopropyl Betaine[4] | 8.000 |
| Methylchloroisothiazolinone and Methylisothiazolinone[5] | 0.100 |
| Citric Acid (40%) | 0.500 |

6) EDETA B POWDER; trademark and origin: BASF
7) CARBOPOL AQUA SF-1 POLYMER; trademark and origin: NOVEON
8) ZETESOL AO 328 U; trademark and origin: ZSCHIMMER & SCHWARZ
9) TEGO-BETAIN F 50; trademark and origin: GOLDSCHMIDT
10) KATHON CG; tradeark and origin: ROHM & HASS The transparent shower gel was prepared by adding 0.5 to 1.5% by weight, relative to the total weight of the shower gel, of the invention's composition of example 23 into the unperfumed shower gel formulation of Table 10 under gentle shaking.

The invention claimed is:

1. A compound of formula

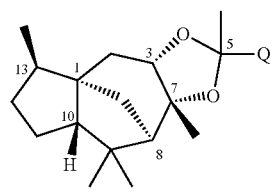

(I)

in the form of any one of its stereoisomers or a mixture thereof, and wherein the Q group represents a —CH=CH—CH$_3$ group or a —C≡C—CH$_3$ group.

2. The compound according to claim 1, characterized in that the Q group is a —CH=CH—CH$_3$ group.

3. The compound according to claim 2, characterized in that compound (I) is in the form of a mixture consisting of isomers E and Z and wherein said isomer E represents at least 75% of the total mixture and isomer Z represents at most 25% of the total mixture.

4. The compound according to claim 3, characterized in that the double bond is in the E configuration.

5. The compound according to claim 1, characterized in that the compound of formula (I) is in the form of a mixture of isomers comprising at least 55% of isomers with a R configuration on carbon 5 and at most 45% of isomers with a S configuration on carbon 5.

6. The compound according to claim 1, characterized in that the compound of formula (I) is in the form of a mixture of isomers comprising at least 70% of isomers with a R configuration on carbon 5 and at most 30% of isomers with a S configuration on carbon 5.

7. The compound according to claim 1, characterized in that the compound of formula (I) is in the form of a mixture of isomers comprising at least 80% of isomers with a R configuration on carbon 5 and at most 20% of isomers with a S configuration on carbon 5.

8. The compound according to claim 1, characterized in that the compound of formula (I) is (1R,3S,5R,7R,8R,10S,13R)-5,7,9,9,13-pentamethyl-5-[(1E)-1-propen-1-yl]-4,6-dioxatetracyclo [6.5.1.0$^{1,10}$.0$^{3,7}$]tetradecane, (1R,3 S,5S,7R,8R,10S,13R)-5,7,9,9,13-pentamethyl-5-[(1E)-1-propen-1-yl]-4,6-dioxatetracyclo[6.5.1.0$^{1,1o}$ 0.0$^{3,7}$]tetradecane, or a mixture thereof, or (1R,3 S,5R,7R,8R,10S,13R)-5,7,9,9,13-pentamethyl-5-[1-propyn-1-yl]-4,6-dioxatetracyclo [6.5.1.0$^{1,10}$.0$^{3,7}$]tetradecane, (1R,3 S,5S,7R,8R,10S,13R)-5,7,9,9,13-pentamethyl-5-[1-propyn-1-yl]-4,6-dioxatetracyclo[6.5.1.0$^{1,10}$0.0$^{3,7}$]tetradecane, or a mixture thereof.

9. A method to confer, enhance, improve or modify odor properties of a perfuming composition or of a perfumed article, the method comprising adding to said composition or article an effective amount of at least a compound of formula (I) as defined in claim 1.

10. A perfuming composition comprising
   i) at least one compound of formula (I), as defined in claim 1;
   ii) at least one ingredient selected from the group consisting of a perfumery carrier and a perfumery base; and
   iii) optionally at least one perfumery adjuvant.

11. A perfumed consumer product comprising at least one compound of formula (I), as defined in claim 1.

12. The perfumed consumer product according to claim 11, characterized in that the perfumed consumer product is a perfume, a fabric care product, a body-care product, a cosmetic preparation, a skin-care product, an air care product, or a home care product.

13. The perfumed consumer product according to claim 12, characterized in that the perfumed consumer product is a fine perfume, a splash or eau de parfum, a cologne, an shave or after-shave lotion, a liquid or solid detergent, a fabric softener, a fabric refresher, an ironing water, a paper, a bleach, a carpet cleaner, a curtain-care product, a shampoo, a coloring preparation, a color care product, a hair shaping product, a dental care product, a disinfectant, an intimate care product, a hair spray, a vanishing cream, a deodorant or antiperspirant, a hair remover, a tanning or sun product, a nail product, a skin cleansing, a makeup, a perfumed soap, a shower or bath mousse, an oil or a gel, or a foot/hand care product, a hygiene product, an air freshener, a "ready to use" powdered air freshener, a mold remover, a furnisher care, a wipe, a dish detergent or a hard-surface detergent, a leather care product, or a car care product.

14. A compound of formula

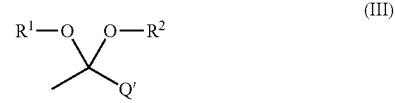

(III)

in the form of any one of its stereoisomers or a mixture thereof, and wherein Q' represents a —CH=CH—CH$_3$ group or a —C≡C—CH$_3$ group; and R$^1$ and R$^2$ group represent, independently from each other, a C$_{1-3}$ alkyl group or R$^1$ and R$^2$ group represent, when taken together, a C$_{2-3}$ alkanediyl; provided that 4,4-diethoxy-2-pentyn e, 2-Methyl-2-(1-propyn-1-yl)-1,3-dioxolane, and 2-methyl-2-(1-propenyl) 1,3-Dioxolane are excluded.

15. A perfumed consumer product comprising a perfuming composition as defined in claim 10.

16. The perfumed consumer product according to claim 15, characterized in that the perfumed consumer product is a perfume, a fabric care product, a body-care product, a cosmetic preparation, a skin-care product, an air care product, or a home care product.

17. The perfumed consumer product according to claim 15, characterized in that the perfumed consumer product is a fine perfume, a splash or eau de parfum, a cologne, an shave or after-shave lotion, a liquid or solid detergent, a fabric softener, a fabric refresher, an ironing water, a paper, a bleach, a carpet cleaner, a curtain-care product, a shampoo, a coloring preparation, a color care product, a hair shaping product, a dental care product, a disinfectant, an intimate care product, a hair spray, a vanishing cream, a deodorant or antiperspirant, a hair remover, a tanning or sun product, a nail product, a skin cleansing, a makeup, a perfumed soap, a shower or bath mousse, an oil or a gel, or a foot/hand care product, a hygiene product, an air freshener, a "ready to use" powdered air freshener, a mold remover, a furnisher care, a wipe, a dish detergent or a hard-surface detergent, a leather care product, or a car care product.

* * * * *